(12) United States Patent
Inoue

(10) Patent No.: US 9,107,634 B2
(45) Date of Patent: Aug. 18, 2015

(54) ULTRASONIC DIAGNOSTIC APPARATUS AND METHOD OF DISPLAYING ULTRASONIC IMAGE

(75) Inventor: Shinsuke Inoue, Tokyo (JP)

(73) Assignee: HITACHI MEDICAL CORPORATION, Tokyo (JP)

( * ) Notice: Subject to any disclaimer, the term of this patent is extended or adjusted under 35 U.S.C. 154(b) by 156 days.

(21) Appl. No.: 13/820,559

(22) PCT Filed: Jul. 28, 2011

(86) PCT No.: PCT/JP2011/067190
§ 371 (c)(1),
(2), (4) Date: Mar. 4, 2013

(87) PCT Pub. No.: WO2012/039192
PCT Pub. Date: Mar. 29, 2012

(65) Prior Publication Data
US 2013/0158400 A1    Jun. 20, 2013

(30) Foreign Application Priority Data

Sep. 21, 2010 (JP) ................................ 2010-211162

(51) Int. Cl.
*A61B 8/00* (2006.01)
*A61B 8/14* (2006.01)
*A61B 8/08* (2006.01)

(52) U.S. Cl.
CPC . *A61B 8/463* (2013.01); *A61B 8/14* (2013.01); *A61B 8/4461* (2013.01); *A61B 8/466* (2013.01); *A61B 8/467* (2013.01); *A61B 8/485* (2013.01); *A61B 8/5207* (2013.01);

(Continued)

(58) Field of Classification Search
CPC .......... A61B 8/14; A61B 8/463; A61B 8/466; A61B 8/467; A61B 8/4461
USPC .................................. 600/437, 438, 443, 479
See application file for complete search history.

(56) References Cited

U.S. PATENT DOCUMENTS

2006/0052702 A1*   3/2006   Matsumura et al. .......... 600/443
2007/0073145 A1*   3/2007   Fan et al. ...................... 600/437

(Continued)

FOREIGN PATENT DOCUMENTS

CN    101150990 A    3/2008
JP    A-2000-60853    2/2000

(Continued)

OTHER PUBLICATIONS

Jun. 27, 2014 Chinese Office Action issued in Chinese Application No. 201180044986.7.

(Continued)

*Primary Examiner* — Baisakhi Roy
(74) *Attorney, Agent, or Firm* — Oliff PLC

(57) ABSTRACT

To provide an ultrasonic diagnostic apparatus capable of producing a three-dimensional image of an object for an organ region within a range of elasticity values desired by an operator and allowing the operator to recognize the region easily, elasticity value data included in a desired elasticity value range among elasticity value data constituting a volume data are selected and rendered. Whereby, a three-dimensional elasticity image in the set elasticity value range is produced. An area corresponding to the elasticity value range is displayed on at least one of a two-dimensional elasticity image and a section image.

14 Claims, 12 Drawing Sheets

(52) U.S. Cl.
CPC .............. *A61B 8/5223* (2013.01); *A61B 8/54* (2013.01); *A61B 8/469* (2013.01); *A61B 8/483* (2013.01)

(56) References Cited

U.S. PATENT DOCUMENTS

| | | |
|---|---|---|
| 2007/0112270 A1 | 5/2007 | Waki et al. |
| 2007/0167784 A1* | 7/2007 | Shekhar et al. ............... 600/443 |
| 2008/0081993 A1* | 4/2008 | Waki ............................ 600/438 |
| 2009/0149750 A1 | 6/2009 | Matsumura |
| 2010/0121192 A1* | 5/2010 | Nogata et al. ................. 600/443 |
| 2010/0149174 A1* | 6/2010 | Nakao et al. .................. 345/419 |
| 2011/0054314 A1* | 3/2011 | Tanigawa et al. ............. 600/438 |
| 2011/0178404 A1 | 7/2011 | Waki |
| 2011/0216958 A1* | 9/2011 | Satoh et al. ................... 382/131 |
| 2012/0215114 A1* | 8/2012 | Gratton et al. ................ 600/479 |

FOREIGN PATENT DOCUMENTS

| | | |
|---|---|---|
| JP | A-2008-259605 | 10/2008 |
| JP | A-2008-284287 | 11/2008 |
| WO | WO 2005/048847 A1 | 6/2005 |
| WO | WO 2010/020921 A2 | 2/2010 |
| WO | WO 2010/026823 A1 | 3/2010 |

OTHER PUBLICATIONS

International Search Report issued in International Application No. PCT/JP2011/067190 dated Oct. 25, 2011.

* cited by examiner

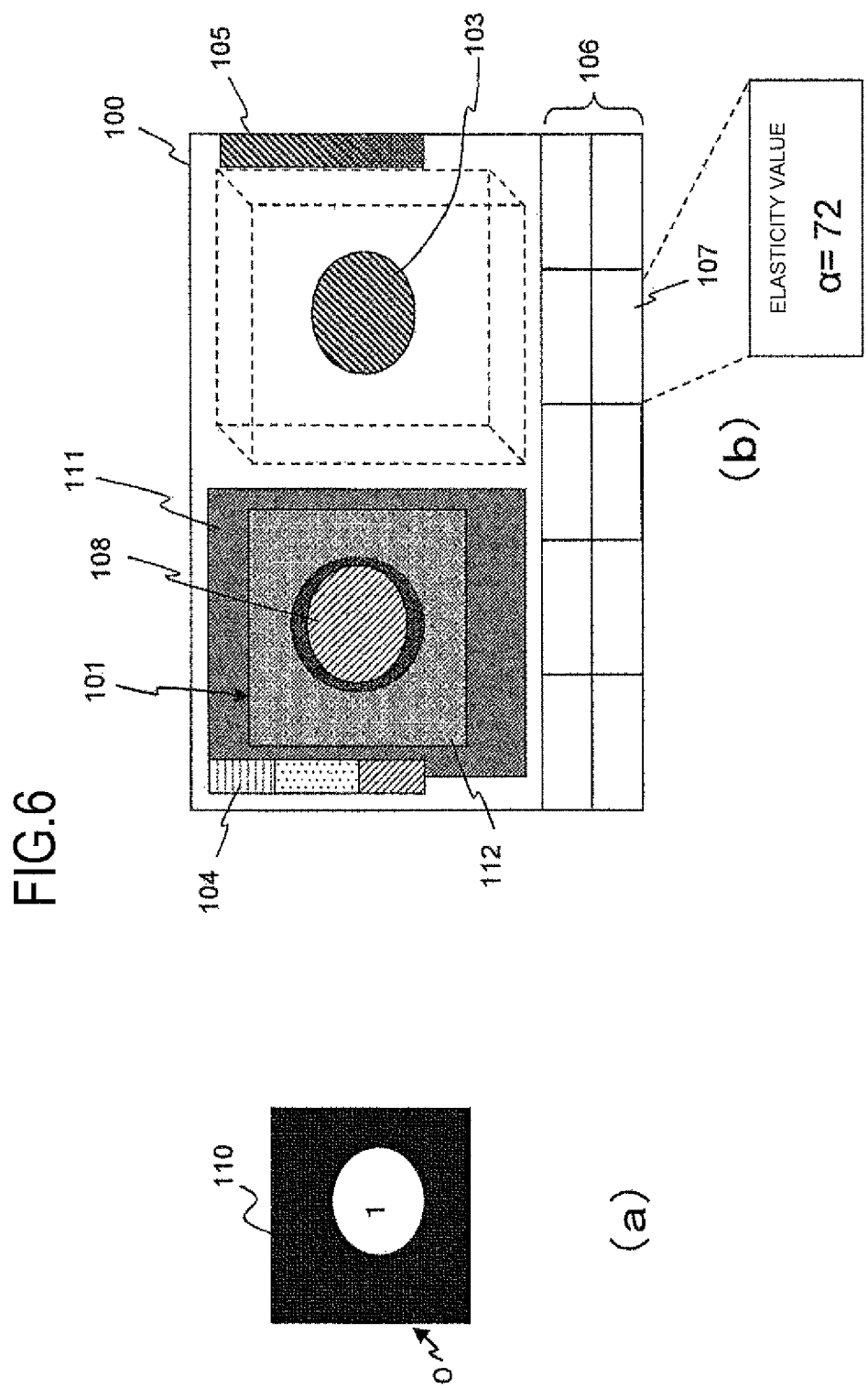

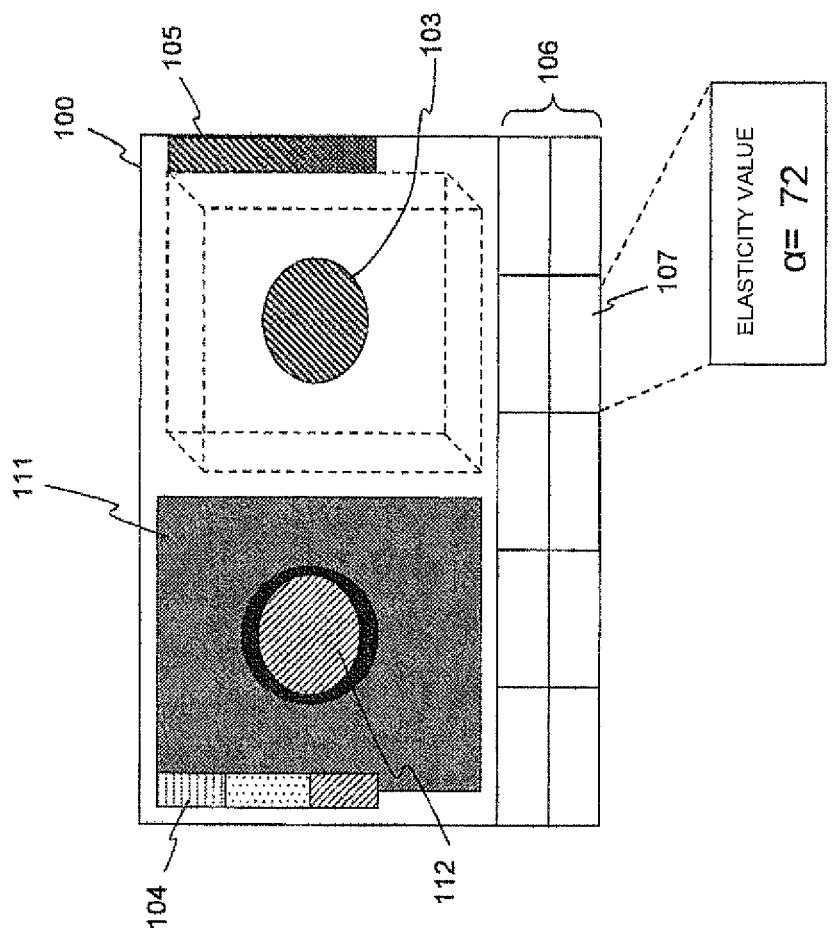

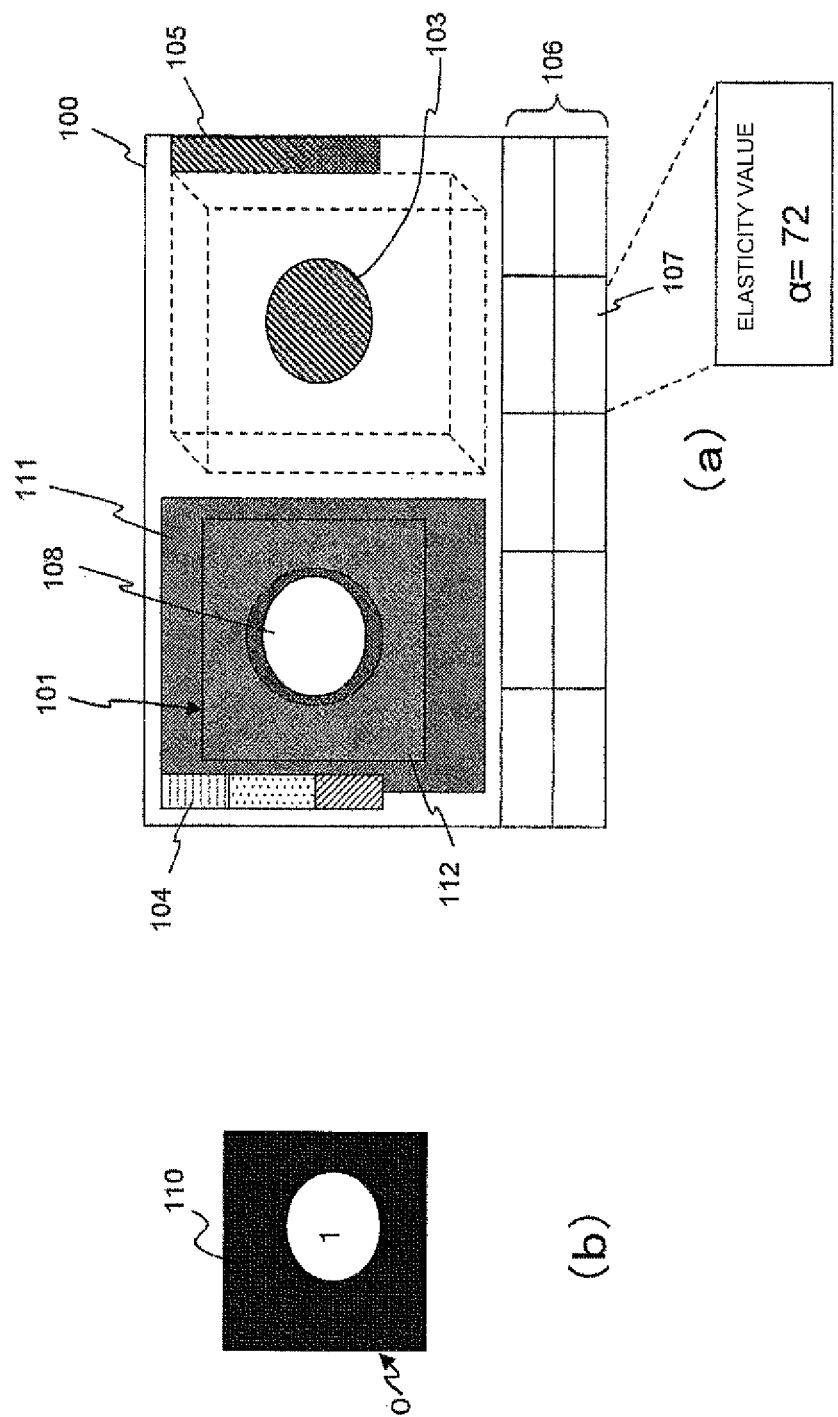

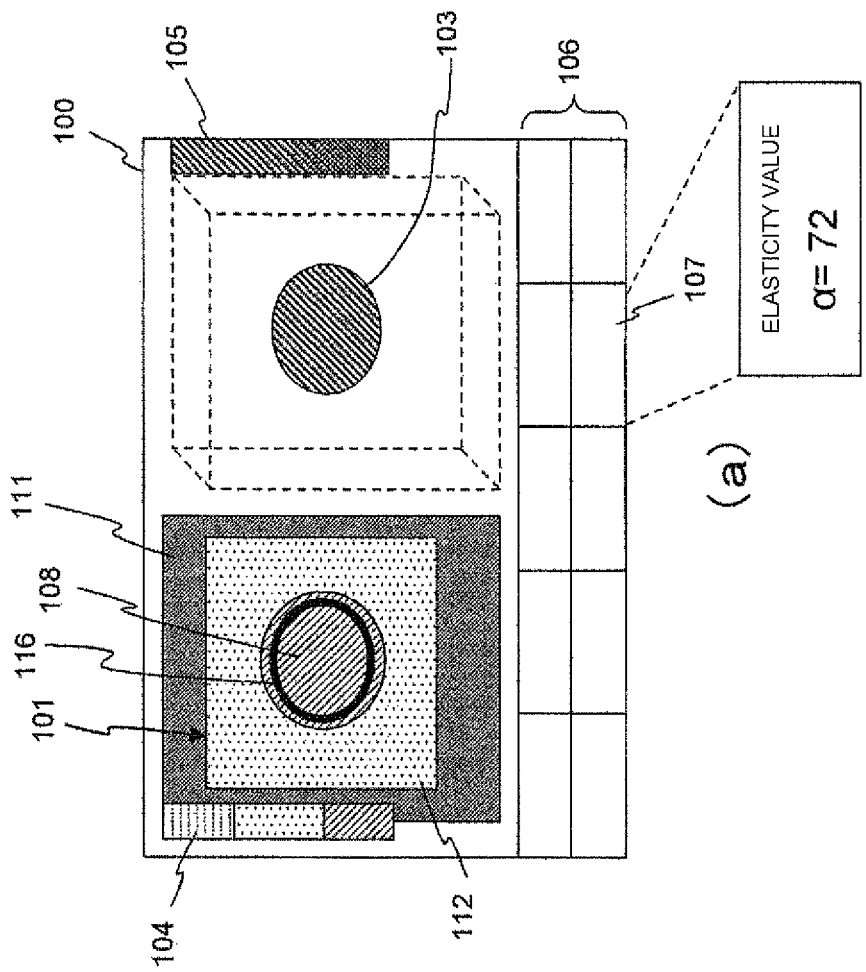
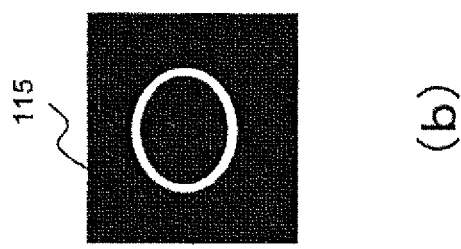

ULTRASONIC DIAGNOSTIC APPARATUS AND METHOD OF DISPLAYING ULTRASONIC IMAGE

TECHNICAL FIELD

The present invention relates to an ultrasonic diagnostic apparatus which uses ultrasonic waves to display an ultrasonic image of a diagnostic part within an object, and more particularly, to an ultrasonic diagnostic apparatus capable of displaying an elasticity image representing the hardness of a living organ of the object as a three-dimensional image.

BACKGROUND ART

As described in Patent Literatures 1 and 2, a conventional ultrasonic diagnostic apparatus transmits ultrasonic into an object, receives the ultrasonic reflection echo signal of a living organ from the reflected wave, performs signal processing on the signal to produce and display a monochrome section image (B mode image) of a diagnostic part having intensities as the ultrasonic reflectivities.

Patent Literature 2 has disclosed a technique involving performing three-dimension coordinate conversion from the monochrome section image and its taking position to obtain three-dimensional volume data including a plurality of section image data items arranged three-dimensionally and then performing volume rendering thereof to provide a monochrome three-dimensional image of a diagnostic part viewed from an arbitrary direction of line of sight. A disclosed technique of the rendering includes providing an opacity for each of voxels constituting the three-dimensional volume data in accordance with the value of the intensity of the voxel, sequentially accumulating the intensity values of the voxels on the line of sight until the accumulated value of the opacities of the voxels arranged on the line of sight reaches one, and using the accumulated intensity value as a pixel value on a two-dimensional projection plane.

Patent Literatures 1 and 2 have also disclosed a technique of determining an elasticity image of a diagnostic part. First, two frames of the monochrome section image are selected, block matching or the like is performed to determine the displacement of each point on the image between the two frames, the determined displacement is subjected to known calculations to determine the elasticity value (such as strain and coefficient of elasticity) representing the hardness for each point on the image. The magnitude of the determined elasticity value is converted into hue information based on a color conversion table to obtain the two-dimensional elasticity image representing the elasticity value as the hue.

In addition, Patent Literature 2 has disclosed a technique in which, in order to solve the problem of being incapable of obtaining a three-dimensional image of an inner lesion portion hidden by outer voxels having high opacities in a three-dimensional gray-scale image, an opacity is provided for each of voxels in three-dimensional volume data obtained from the monochrome section image in accordance with the magnitude of the elasticity value to perform volume rendering. This can provide the three-dimensional gray-scale image showing a hard organ more opaquely and a soft organ more transparently.

In Patent Literature 2, a plurality of two-dimensional elasticity images are coordinate-converted into three-dimensional volume data which is then subjected to volume rendering to produce a three-dimensional elasticity image. In the typical rendering method in which voxel values are simply accumulated, a problem occurs in which the elasticity values are accumulated to provide the three-dimensional elasticity image including distorted elasticity characteristics of a living organ, so that the intensity data of the monochrome section image is used to determine the voxel having the highest contribution on the line of sight, and the elasticity value of that voxel is used as the elasticity value of the two-dimensional projection plane to produce the three-dimensional elasticity image.

For the display method, the monochrome section image (two-dimensional) and the two-dimensional elasticity image are displayed one on the other in Patent Literature 1. In Patent Literature 2, the monochrome three-dimensional image and the three-dimensional elasticity image are superimposed into one image which is then displayed together with the monochrome section images in three directions on one screen.

Patent Literature 3 has disclosed displaying a monochrome section image and a two-dimensional elasticity image together on one screen and superimposing and displaying the monochrome section image on the two-dimensional elasticity image.

PRIOR ART REFERENCES

Patent Literature

Patent Literature 1: WO2005/048847
Patent Literature 2: JP-A-2008-259605
Patent Literature 3: JP-A-2000-60853

SUMMARY OF THE INVENTION

Problems that the Invention is to Solve

In the method in which the opacity is provided for each of the voxels in the three-dimensional volume data obtained from the monochrome section image in accordance with the magnitude of the elasticity value to perform the volume rendering to produce the three-dimensional image or in the method in which the intensity data of the monochrome section image is used to determine the voxel having the highest contribution on the line of sight and the elasticity value of that voxel is used as the elasticity value of the two-dimensional projection plane to produce the three-dimensional elasticity image as in the technique described in Patent Literature 2, a three-dimensional elasticity image including only organs having elasticity values within an arbitrary range can not be obtained. In addition, an operator has difficulty in recognizing the range of elasticity values of the diagnostic part from the displayed three-dimensional image and three-dimensional elasticity image obtained in the conventional method. Furthermore, even when the three-dimensional image and the three-dimensional elasticity image are displayed together with the monochrome section image, a problem occurs in which the operator has difficulty in recognizing which area of the monochrome section image is displayed as the three-dimensional image or the three-dimensional elasticity image.

It is an object of the present invention to provide an ultrasonic diagnostic apparatus capable of producing a three-dimensional image of an organ region of an object having elasticity values within a range desired by an operator and allowing the operator to recognize the region easily.

Means for Solving the Problems

To achieve the above object, according to an aspect, the present invention provides an ultrasonic diagnostic apparatus as described below. The ultrasonic diagnostic apparatus includes a section image constituting unit which transmits ultrasonic into an object and produces a section image of the object based on a received signal and a two-dimensional elasticity image constituting unit which processes the signal to produce a two-dimensional elasticity image of an elasticity value representing elasticity, a rendering unit which produces volume data from a plurality of the two-dimensional elasticity images and selects and renders elasticity value data of the volume data included in a desired elasticity value range to produce a three-dimensional elasticity image of the elasticity value data in the elasticity value range, and a display unit which displays the three-dimensional elasticity image and at least one of the two-dimensional elasticity image and the section image showing an area corresponding to the elasticity value range.

The display unit can display an area of the two-dimensional elasticity image outside the elasticity value range with a mask placed thereon. For example, the display unit displays a combined image provided by adding the two-dimensional elasticity image and the section image at a ratio, the ratio in an area within the elasticity value range being different from the ratio in the area with the mask placed thereon. In this case, the display unit can display the combined image provided by adding the two-dimensional elasticity image at the ratio set at zero in the area with the mask placed thereon.

The display unit can display an area of the two-dimensional elasticity image within the elasticity value range or the area with the mask placed thereon filled in with a single hue. For example, the single hue is set in accordance with an elasticity value in the area of the two-dimensional elasticity image to be filled in with the hue.

The display unit can display a line representing an outline of the elasticity value range in the two-dimensional elasticity image.

The ultrasonic diagnostic apparatus can further include an operation unit which is used by an operator to set the elasticity value range. When the operation unit receives setting of the elasticity value range, the display unit can display the area corresponding to the elasticity value range on at least one of the two-dimensional elasticity image and the section image only for a predetermined time period.

When the two-dimensional elasticity image is a color image having a different hue provided in accordance with an elasticity value, the display unit can display a color map representing the relationship between the elasticity value and the hue by adding a display showing the elasticity value range thereto. Alternatively, the display unit can display the elasticity value range with a numeric value by adding a hue corresponding to the elasticity value range thereto.

According to another aspect, the present invention provides a method of displaying an ultrasonic image as described below. The method includes transmitting ultrasonic into an object and producing a section image of the object based on a received signal, processing the signal to produce a two-dimensional elasticity image of an elasticity value representing elasticity, producing volume data from a plurality of the two-dimensional elasticity images. Elasticity value data of the volume data included in a desired elasticity value range is selected and rendered to produce a three-dimensional elasticity image of the elasticity value data in the elasticity value range. The three-dimensional elasticity image and at least one of the two-dimensional elasticity image and the section image showing an area corresponding to the elasticity value range are displayed.

Advantage of the Invention

According to the present invention, since the area of the object organ corresponding to the elasticity value range displayed as the three-dimensional elasticity image can be visually shown on at least one of the section image and the two-dimensional elasticity image, the operator can easily recognize that area. The setting of the elasticity value range can readily provide the three-dimensional elasticity image in the desired area.

BRIEF DESCRIPTION OF THE DRAWINGS

FIG. 6 (a) An explanatory view showing a mask 110 produced in Embodiment 1, and (b) an explanatory view showing an example of the screen produced in Embodiment 1.

FIG. 7 An explanatory view showing an example of the screen produced in Embodiment 2.

FIG. 8 (a) An explanatory view showing an example of the screen produced in Embodiment 3, and (b) an explanatory view showing the mask 110 produced in Embodiment 3.

FIG. 9 (a) An explanatory view showing an example of the screen produced in Embodiment 4, and (b) an explanatory view showing the mask 110 produced in Embodiment 4.

BEST MODE FOR CARRYING OUT THE INVENTION

An ultrasonic diagnostic apparatus according to an embodiment of the present invention will hereinafter be described with the accompanying drawings. In the present embodiment, a B mode image representing the distribution of ultrasonic reflectivities of organs in a predetermined section of an object is referred to as a monochrome section image, a two-dimensional projection image provided by rendering volume data formed of the data of the monochrome section image is referred to as a three-dimensional image, an image representing the two-dimensional distribution of elasticity values indicating the elasticity of organs of the object in a predetermined section is referred to as a two-dimensional elasticity image, and a two-dimensional projection image provided by rendering volume data formed of the data of the two-dimensional elasticity image is referred to as a three-dimensional elasticity image.

Figure 1:
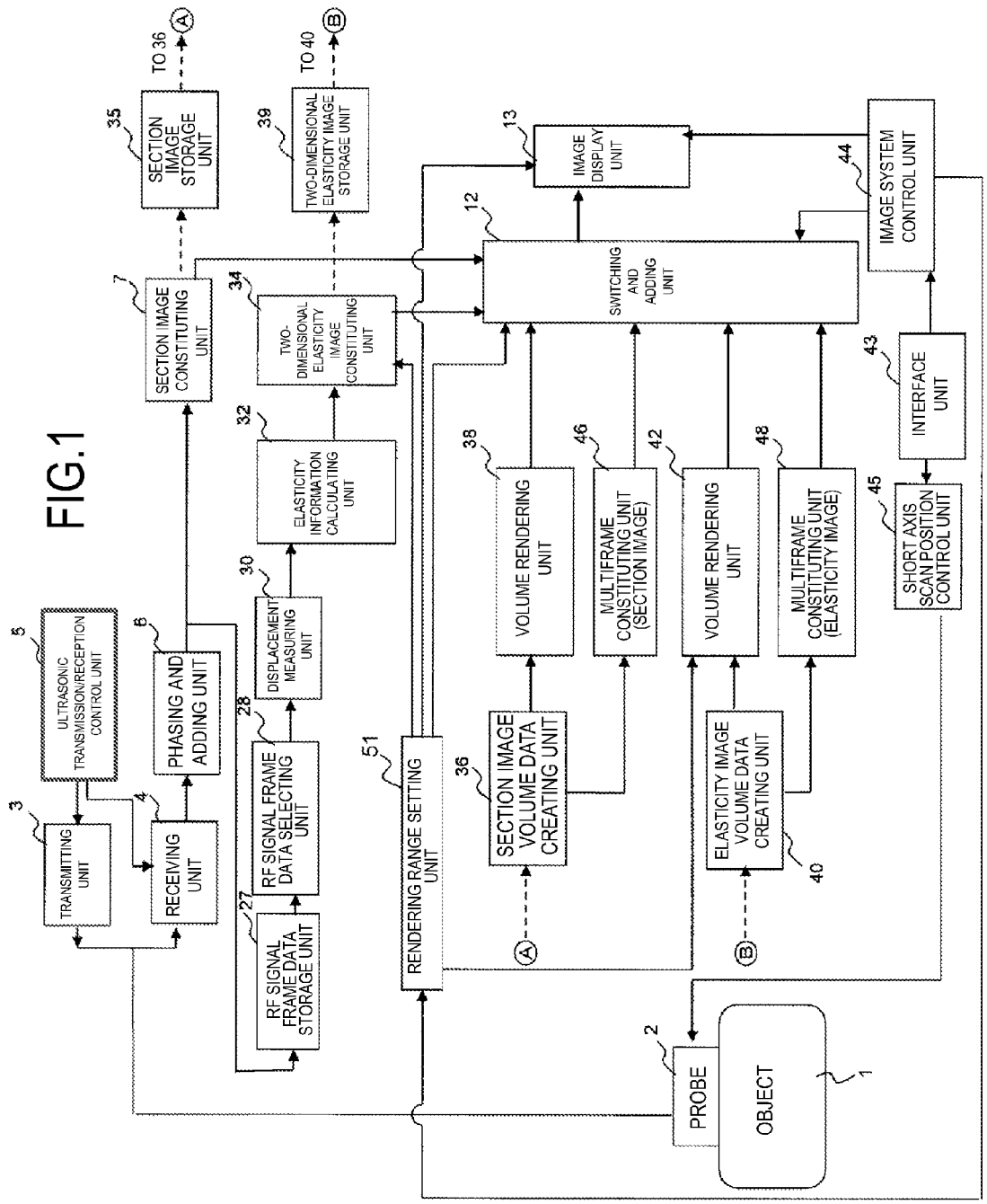
FIG. 1 A block diagram showing the configuration of an ultrasonic diagnostic apparatus according to an embodiment.

As shown in FIG. 1, the ultrasonic diagnostic apparatus includes a probe 2 which is brought into contact with an object 1 for use, a transmitting unit 3 which repeatedly transmits ultrasonic at predetermined time intervals to a diagnostic part within the object 1 through the probe 2, a receiving unit 4 which receives a reflection echo signal reflected by the object 1 on the time series, an ultrasonic transmission/reception control unit 5, and a phasing and adding unit 6 which phases and adds the received reflection echo.

The probe 2 includes a plurality of oscillators arranged in line or in fan form, and the oscillators transmit and receive the ultrasonic to and from the object 1. The probe 2 has the function of mechanically scanning the plurality of oscillators in a direction (short axis direction) orthogonal to the arrangement direction of the oscillators to allow three-dimensional transmission and reception of the ultrasonic. Alternatively, the probe 2 may be provided by using a plurality of oscillators arranged two-dimensionally to transmit and receive the ultrasonic three-dimensionally without mechanically moving the oscillators.

The transmitting unit 3 produces a transmission wave pulse for driving the probe 2 to generate the ultrasonic. The transmitting unit 3 controls the phase of the transmission wave signal passed to each of the oscillators of the probe 2 to set the convergence point of the ultrasonic to be transmitted at a certain depth. The receiving unit 4 amplifies the reflection echo signal received by each of the oscillators of the probe 2 with a predetermined gain to produce an RF signal, that is, a reception wave signal. The ultrasonic transmission/reception control unit 5 controls the transmitting unit 3 and the receiving unit 4. The phasing and adding unit 6 matches the phases of the RF signals and then adds them to form an ultrasonic beam converged to a single or a plurality of convergence points to produce RF signal frame data (corresponding to RAW data).

The ultrasonic diagnostic apparatus also includes an interface unit 43 which receives the settings from the operator, an image display unit 13, a switching and adding unit 12 which switches types of the image to be displayed on the image display unit 13, an image system control unit 44, short axis scan position control unit 45. The short axis scan position control unit 45 controls the operation of the probe 2 to mechanically scan the plurality of oscillators in the direction orthogonal to the arrangement direction to perform three-dimensional transmission and reception in a predetermined range.

The ultrasonic diagnostic apparatus also includes a section image constituting unit 7, a section image storage unit 35, a section image volume data creating unit 36, a volume rendering unit 38, and a multiframe constituting unit (section image) 46, as components for producing a monochrome section image and a three-dimensional image of a diagnostic part having intensities as ultrasonic reflectivities from the RF frame data. In addition, the ultrasonic diagnostic apparatus includes an RF signal frame data storage unit 27, an RF signal frame data selecting unit 28, a displacement measuring unit 30, an elasticity information calculating unit 32, an elasticity image constituting unit 34, a two-dimensional elasticity image storage unit 39, an elasticity image volume data creating unit 40, a volume rendering unit 42, a multiframe constituting unit (elasticity image) 48, and a rendering range setting unit 51, as components for producing a two-dimensional elasticity image and a three-dimensional elasticity image from the RF signal frame data.

The section image constituting unit 7 performs gain correction, log compression, detection, outline enhancement, filtering and the like on the RF signal frame data produced in the phasing and adding unit 6 to produce the monochrome section image (B mode image) of the diagnostic part having the intensities (shades) as the reflectivities. At this point, the image system control unit 44 receives the conditions of producing the monochrome section image from the operator through the interface unit 43 to control the section image constituting unit 7.

The section image storage unit 35 stores the monochrome section image constituted by the section image constituting unit 7 and its taking position in correspondence with each other. The taking position refers to the movement amount in the short axis direction under control of the short axis scan position control unit 45. The volume data creating unit 36 performs coordinate conversion for replacement in accordance with the movement amount in the short axis direction on a plurality of monochrome section images (for one volume) stored in the section image storage unit 35 to create three-dimensional volume data.

The volume rendering unit 38 performs volume rendering of the three-dimensional volume data produced by the volume data creating unit 36 based on the intensity and the opacity using the following expressions (1) to (3) to constitute the three-dimensional image of the diagnostic part of the object (two-dimensional projection image of three-dimensional volume data). The projection direction (direction of line of sight) is received by the image system control unit 44 from the operator through the interface unit 43.

$$\mathrm{Cout}(i) = \mathrm{Cout}(i-1) + (1 - A\mathrm{out}(i-1))A(i)C(i)S(i) \qquad \text{expression (1)}$$

$$A\mathrm{out}(i) = A\mathrm{out}(i-1) + (1 - A\mathrm{out}(i-1))A(i) \qquad \text{expression (2)}$$

$$A(i) = \mathrm{Bopacity}[C(i)] \qquad \text{expression (3)}$$

In the expression (1), Cout(i) represents the value output as the pixel value of the two-dimensional projection plane. C(i) represents the intensity value of an ith voxel (where i=0 to N−1) present on the line of sight when the three-dimensional image is viewed from a certain point on the two-dimensional projection plane. The voxel refers to the position of each of intensity data items constituting the three-dimensional volume data. When N voxels are arranged on the line of sight, the intensity value Cout(N−1) calculated by accumulating the intensity values of the voxels (i=0 to N−1) with the expression (1) is the pixel value to be output finally. Cout(i−1) represents the accumulated value up to an i−1th voxel.

A(i) in the expression (1) represents the opacity of the ith voxel present on the line of sight and takes values ranging from 0 to 1.0. The opacity A(i) is determined in accordance with the magnitude of the intensity value of the voxel by referencing a table (Bopacity[C(i)] defining the predefined relationship between intensity value C(i) and opacity or by substituting the intensity value C(i) into a function (Bopacity [C(i)] defining the predefined relationship between the intensity value C (i) and opacity as shown in the expression (3). For example, a higher opacity is provided for a voxel having a higher intensity value. The opacity thus provided in accordance with the intensity value determines the contribution of the intensity value C(i) of the voxel to the intensity value Cout(N−1) of the two-dimensional projection plane to be output.

Aout(i) in the expression (2) is the value calculated by accumulating the opacities A(i) provided from the expression (3) in accordance with the right side of the expression (2) up to the ith voxel. In the expression (1), the accumulated value Aout(i−1) of the opacities up to the i−1th voxel calculated as in the expression (2) is used. As apparent from the expression (2), Aout (i) is accumulated each time the voxel is passed, and is converged to 1.0. Thus, when the accumulated value Aout (i−1) of the opacities up to the i−1th voxel is approximately 1.0 as shown in the above expression (1), the second term in the right side of the expression (1) is 0, and the intensity value C(i) of the ith and subsequent voxels is not reflected in the two-dimensional projection image (three-dimensional) to be output. The initial values of Cout(i) and Aout(i) are zero.

S(i) in the expression (1) is a weight component for shading and is calculated from the slope of the intensity value determined from the intensity value. C(i) and its surrounding intensity values. For example, when the normal to the plane centered on the ith voxel (slope of the intensity value) matches the optical axis of a predefined light source, the light is reflected most strongly and thus 1.0 is provided as S(i) for the voxel i based on a predefined table and function. When the light source is orthogonal to the normal, 0.0 is provided as S(i). This provides the shading for the obtained two-dimensional projection image to achieve a highlighting effect.

The multiframe constituting unit (section image) 46 produces a monochrome section image on an arbitrary section from the three-dimensional volume data created by the volume data creating unit 36. The position of the arbitrary section is received by the interface unit 43 from the operator and is set in the multiframe constituting unit (section image) 46 through the image system control unit 44. A plurality of positions of the arbitrary sections may be set, and the multiframe constituting unit 46 produces the monochrome section image for each of the plurality of positions of the arbitrary sections.

These configurations form the three-dimensional image of the diagnostic part of the object 1 and the monochrome section image of the arbitrary section.

The RF signal frame data produced by the phasing and adding unit 6 is sequentially stored in the RF signal frame data storage unit 27. For example, the RF signal frame data storage unit 27 sequentially stores the RF signal data produced on the time series, that is, on the basis of the frame rate of the image, from the phasing and adding unit 6 in a frame memory. The RF signal frame data selecting unit 28 selects a set, that is, two RF signal frame data items from the plurality of RF signal frame data items stored in the RF signal frame data storage unit 27. For example, in response to an instruction from the image system control unit 44, the RF signal frame data selecting unit 28 selects the last stored RF signal frame data (N) as first data, and selects one RF signal frame data (X) from a group of RF signal frame data (N−1, N−2, N−3, ..., N−M) stored previously. N, M, and X represent index numbers provided for the RF signal frame data items and are natural numbers.

The displacement measuring unit 30 determines a displacement or the like of a living organ from a set of RF signal frame data items.

For example, the displacement measuring unit 30 performs one-dimensional or two-dimensional correlation processing on the set of data items, that is, the RF signal frame data (N) and the RF signal frame data (X) selected by the RF signal frame data selecting unit 28 to determine one-dimensional or two-dimensional displacement distribution for a displacement and a movement vector (direction and magnitude of displacement) in the living organ for each point in the section image (two-dimensional reflectivity image). A block matching method is used for detecting the movement vector. The block matching method includes dividing the section image into blocks each constituting of N pixels by N pixels, for example, focusing on a block within an area of interest, searching the previous frame for a block having the reflectivity distribution most approximate to that of the focused block, and referencing that block to determine a sample value through predictive coding, that is, differences.

The elasticity information calculating unit 32 performs predetermined calculations based on the displacement and the movement vector determined by the displacement measuring unit to calculate the elasticity value and outputs it as time-series elasticity frame data. The elasticity value mentioned herein may be a value representing the elasticity of the organ of the object 1, and examples thereof include strain, coefficient of elasticity, displacement, viscosity, strain ratio and the like. When the strain is used as the elasticity value, it can be calculated by spatial differentiation of the movement amount of the living organ, for example, displacement.

The two-dimensional elasticity image constituting unit 34 includes a frame memory and an image processing unit, and stores the elasticity frame data output on the time series from the elasticity information calculating unit 32 in the frame memory and processes the stored frame data in the image processing unit to produce the two-dimensional elasticity image representing the two-dimensional distribution of the elasticity values in the diagnostic part of the object. The two-dimensional elasticity image is a color image provided by converting the elasticity values into hue information based on a predefined color conversion table. For example, as the elasticity value is changed from a predetermined small value toward a larger value, the hue is given in 255 levels (1 to 255) gradually changing from blue (B) to green (G), and then red (R). The elasticity value at the hardest part is one, and the elasticity value at the softest part is 255.

The two-dimensional elasticity image storage unit 39 stores the two-dimensional elasticity image produced in the elasticity image constituting unit 34 and its taking position in correspondence with each other. The volume data creating unit 40 performs three-dimensional coordinate conversion based on the two-dimensional elasticity image stored in the two-dimensional elasticity image storage unit 39 and its taking position to produce three-dimensional volume data including the plurality of spatially contiguous two-dimensional elasticity images placed three-dimensionally.

In the present embodiment, in order to obtain the three-dimensional image allowing the operator to clearly recognize the shape of the organ having the elasticity values within the range desired by the operator, only the voxels having the elasticity values within the range desired by the operator are rendered out of the voxels constituting the three-dimensional volume data. This can provide the three-dimensional elasticity image of the organ having the elasticity values within the range set by the operator.

The setting of the range of the elasticity values is received by the rendering range setting unit 51 from the operator through the interface unit 43. Examples of the setting method include setting the range of the elasticity values for the rendering at the range from a single value set by the operator to 1 which is the value representing the hardest elasticity (1 to a) in the values from 1 to 255 since the range of the elasticity values includes the 255 levels, setting the range of the elasticity values for the rendering at the range from a single value set by the operator to 255 which is the value representing the softest elasticity (a to 255), and setting the range for the rendering at the range between two elasticity values set by the operator. In the following, description is made of the example in which the rendering is performed in the range from a single value set by the operator to 1 which is the value representing the hardest elasticity. FIG. 2(c) is an enlarged view showing the elasticity value α set by the operator and displayed in an area 107.

The volume rendering unit 42 selects the voxels having the elasticity value data included in the range set in the rendering range setting unit 51 from the elasticity volume data, and performs the volume rendering only on those voxels to constitute the three-dimensional elasticity image. Since this can provide the three-dimensional elasticity image of the voxels having the elasticity values within the range desired by the operator, the operator can recognize the three-dimensional shape of the hard organ and the soft organ present inside the voxels having high opacities.

The methods of selecting the voxels having the elasticity values within the range include replacing the elasticity value data outside the range set in the rendering range setting unit 51 with zero, or placing a mask on the voxels having the elasticity value data outside the set range. The selected voxels are subjected to the volume rendering based on the elasticity values and the opacities using the following expressions (4) to (6). The projection direction (direction of line of sight) is received by the image system control unit 44 from the operator through the interface 43.

$$Eout(i) = Eout(i-1) + (1 - Aout(i-1))A(i)E(i)S(i) \quad \text{expression (4)}$$

$$Aout(i) = Aout(i-1) + (1 - Aout(i-1))A(i) \quad \text{expression (5)}$$

$$A(i) = Eopacity[E(i)] \quad \text{expression (6)}$$

In the expression (4), $Eout(i)$ represents the value output as the pixel value of the projection plane. $E(i)$ represents the elasticity value of an ith voxel (where $i=0$ to $N-1$) present on the line of sight when the three-dimensional elasticity image is viewed from a certain point on the two-dimensional projection plane. When the method of replacing the elasticity value data outside the set range with zero is used as the method of selecting the voxels having the elasticity values within the range, the elasticity value data $E(i)$ outside the range is replaced with zero ($E(i)=0$) to avoid rendering of the elasticity value data outside the predetermined elasticity value range. When the elasticity values of N voxels are arranged on the line of sight, the accumulated value $Eout(N-1)$ calculated by accumulating the elasticity values ($i=0$ to $N-1$) with the expression (4) is the pixel value to be output finally. $Eout(i-1)$ represents the accumulated value up to the i−1th voxel.

$A(i)$ in the expression (4) represents the opacity of the ith voxel present on the line of sight and takes values ranging from 0 to 1.0. The opacity $A(i)$ is determined in accordance with the magnitude of the elasticity value of the voxel by referencing a table ($Eopacity[E(i)]$) defining the predefined relationship between elasticity value $E(i)$ and opacity or by substituting the elasticity value $E(i)$ into a function ($Eopacity[E(i)]$) defining the predefined relationship between the elasticity value $E(i)$ and opacity as shown in the expression (6).

$Aout(i)$ in the expression (5) is the value calculated by accumulating the opacities $A(i)$ provided from the expression (6) in accordance with the right side of the expression (5) up to the ith voxel. In the expression (4), the accumulated value $Aout(i-1)$ of the opacities up to the i−1th voxel calculated as in the expression (5) is used. As apparent from the expression (5), $Aout(i)$ is accumulated each time the voxel is passed, and is converged to 1.0. Thus, when the accumulated value $Aout(i-1)$ of the opacities up to the i−1th voxel is approximately 1.0 as shown in the above expression (4), the second term in the right side of the expression (4) is 0, and the elasticity value $E(i)$ of the ith and subsequent voxels is not reflected in the two-dimensional projection image (three-dimensional) to be output. The initial values of $Eout(i)$ and $Aout(i)$ are zero.

$S(i)$ in the expression (4) is a weight component for shading and is calculated from the slope of the elasticity value determined from the elasticity value $E(i)$ and its surrounding elasticity values. For example, when the normal to the plane centered on the ith voxel (slope of the elasticity value) matches the optical axis of a predefined light source, the light is reflected most strongly and thus 1.0 is provided as $S(i)$ for the voxel i based on a predefined table and function. When the light source is orthogonal to the normal, 0.0 is provided as $S(i)$. This provides the shading for the obtained two-dimensional projection image to achieve a highlighting effect.

In the present embodiment, the three-dimensional elasticity image is colored by referencing a color map 105 for the three-dimensional elasticity image in FIG. 2(d). The color map 105 for the three-dimensional elasticity image provides a hue (single color) in association with the set elasticity value range and provides an intensity (lightness) varying in accordance with the magnitude of the value of $Eout(i)$, for example. Specifically, as the contribution of the weight component $S(i)$ for shading is larger ($S(i)$ is smaller) in the expression (4), $Eout(i)$ is smaller and thus the setting is performed to be closer to black (lower intensity).

By way of example, the hue in association with the set elasticity value range is blue when the average value of the set elasticity value range is smaller than the average value 127 of the elasticity value, or the hue is red when the average value is larger than 127. For example, the blue may be set when the hard range is selected with a soft/hard selecting switch 122, later described, or the red may be set when the soft range is selected. The hue may be associated with the average value of the set elasticity value range.

The setting is performed to be closer to black (lower intensity) as the contribution of $S(i)$ in the expression (4) is larger, that is, as the value of $Eout(i)$ is smaller, so that the shading effect can be achieved to result in the stereoscopic three-dimensional elasticity image.

Another coloring method includes performing the rendering with the opacity $A(i)$ set at 1.0 in the expression (4) so that the value of $Eout(i)$ is maintained at the elasticity value on the surface of the volume data to be rendered. Thus, the coloring can be performed with the hue associated with the elasticity value on the surface of the volume data to be rendered by using a color map similar to a color map 104 for the two-dimensional elasticity image.

The multiframe constituting unit (elasticity image) 48 produces a two-dimensional elasticity image on an arbitrary section from the elasticity volume data. The specification of the arbitrary section is received by the interface unit 43 from the operator and is passed to the multiframe constituting unit 48 through the image system control unit 44. A plurality of positions of the arbitrary sections can be set, and the multiframe constituting unit 48 produces the two-dimensional elasticity image for each of the plurality of positions of the arbitrary sections.

The switching and adding unit 12 is formed of a frame memory, an image processing unit, and an image selecting unit. The frame memory stores the monochrome section images produced by the elasticity image constituting unit 7 and the multiframe constituting unit 46, the color two-dimensional elasticity image produced by the two-dimensional elasticity image constituting unit 34 and the multiframe constituting unit 48, the three-dimensional image produced by the volume rendering unit 38, and the three-dimensional elasticity image produced by the volume rendering unit 48.

The switching and adding unit 12 produces a combined image provided by adding the color two-dimensional elasticity image to the monochrome section image at a predetermined ratio in response to an instruction of the operator. The monochrome section image produced by the elasticity image constituting unit 7 or the monochrome section image on the arbitrary section produced by the multiframe constituting unit 46 is used as the monochrome section image. The two-dimensional elasticity image produced by the two-dimensional elasticity image constituting unit 34 or the two-dimensional elasticity image on the arbitrary section produced by the multiframe constituting unit 48 is used as the color two-dimensional elasticity image. The known method of producing the combined images described in Patent Literature 1 is now described simply. When the intensity value of a pixel at the position x, y in the monochrome section image is represented by C(x,y), the monochrome section image is converted into a color section image. When the output values of red (R), green (G), and blur (B) of the pixel are represented by C(R)(x,y), C(G)(x,y), and C(B)(x,y), the conversion is performed by setting the values of C(x,y) as shown in the following expressions (7) to (9).

$$C(R)(x,y)=C(x,y) \quad \text{expression (7)}$$

$$C(G)(x,y)=C(x,y) \quad \text{expression (8)}$$

$$C(B)(x,y)=C(x,y) \quad \text{expression (9)}$$

When the output values of red (R), green (G), and blue (B) of a pixel at coordinates (x,y) in the color two-dimensional elasticity image are represented by E(R)(x,y), E(G)(x,y), and E(B)(x,y), and the combination ratio set by the operator is represented by r (0<r≤1), the output values D(R)(x,y), D(G)(x,y), and D(B)(x,y) of the pixel in the combined image are determined with the following expressions (10) to (12).

$$D(R)(x,y)=E(R)(x,y)\times r+C(R)(x,y) \quad \text{expression (10)}$$

$$D(G)(x,y)=E(G)(x,y)\times r+C(G)(x,y) \quad \text{expression (11)}$$

$$D(B)(x,y)=E(B)(x,y)\times r+C(B)(x,y) \quad \text{expression (12)}$$

The produced combined image is stored in the frame memory.

The switching and adding unit 12 selects and passes the image to be displayed in the image display unit 13 from the monochrome section image, the color two-dimensional elasticity image, the three-dimensional image, the three-dimensional elasticity image, and the combined image stored in the frame memory in response to an instruction received from the operator through the interface unit 43. The image display unit 13 displays the passed one or more images in a predetermined arrangement on the screen.

The image system control unit 44 controls the respective components involved in the image production. The interface unit 43 receives the hue of the elasticity image (hue on the color map), the setting of ROI (region of interest), the setting of the frame rate or the like from the operator. The image system control unit 44 displays the range of the elasticity values set for producing the three-dimensional elasticity image, the color map for the elasticity image, the values of various set parameters and the like at predetermined positions on the screen in the image display unit 13.

FIG. 2(a) is an example of the image displayed in the image display unit 13. The combined image of the monochrome section image 111 and the two-dimensional elasticity image 112 is displayed in a left area on a screen 100. Since the two-dimensional elasticity image 112 is produced only for an ROI 101 set by the operator, the image 112 is combined with the monochrome section image 111 only in the central area of the display region. The color map 104 showing the relationship between the hue and the elasticity value of the two-dimensional elasticity image 112 is displayed on the left of the two-dimensional elasticity image 112. As shown in the enlarged view of FIG. 2(b), the color map 104 includes a red hue allocated to a soft area with high elasticity values, a blue hue allocated to a hard area with low elasticity values, and a green hue allocated to an intermediate area. The colors are changed stepwise with the elasticity value, and 255 levels are present in total.

The three-dimensional elasticity image 103 is displayed in a right area on the screen 100. The three-dimensional elasticity image 103 is provided by rendering only the voxels within the range of elasticity values set by the operator. The color map 105 for the three-dimensional elasticity image showing the relationship between the hue and the elasticity value of the three-dimensional elasticity image 103 is displayed on the right of the three-dimensional elasticity image 103.

A parameter display area 106 showing the values of various parameters received from the operator is displayed in a lower portion on the screen 100. The parameter display area includes the area 107 showing the range of elasticity values set by the operator as the rendering range. The displayed three-dimensional elasticity image 103 is produced by the rendering unit 42 rendering the voxels in the elasticity value range set as the rendering range.

The interface unit 43 in FIG. 1 includes an operation panel 120 placed under the image display unit 13 as shown in FIG. 3(a). The operation panel 120 includes a toggle switch 121 for setting the elasticity value and the soft/hard selecting switch 122. The soft/hard selecting switch 122 has the configuration as shown in FIG. 4(a). When a button labeled with "hard" is selected, the volume rendering unit 42 selects and renders the voxels in the harder range than the elasticity value α set with the toggle switch 121, that is, in the range from 1 to α to produce and display the three-dimensional elasticity image 103 of the hard organ having the elasticity value of α or lower as shown in FIG. 4(b). On the other hand, when a button labeled with "soft" is selected, the volume rendering unit 42 selects and renders the voxels in the range from a to 255 which is the softer range than the elasticity value α to produce and display the three-dimensional elasticity image 103 of the soft organ having the elasticity value of α or higher as shown in FIG. 4(c).

Embodiment 1

The ultrasonic diagnostic apparatus of Embodiment 1 includes the section image constituting unit 7 which produces the section image of the object using the received signal as a result of the ultrasonic transmitted into the object, the two-dimensional elasticity image constituting unit 34 which processes the signal to produce the two-dimensional elasticity image for the elasticity value representing the elasticity, the rendering unit 42 which produces the volume data formed of the plurality two-dimensional elasticity images, and selects and renders the elasticity value data of the volume data included in the desired elasticity value range to produce the three-dimensional elasticity image for the elasticity value data within the elasticity value range, and the display unit 13 which displays the three-dimensional elasticity image and at least one of the two-dimensional elasticity image and the section image showing the area associated with the elasticity value range. In the method of displaying the ultrasonic image, ultrasonic is transmitted into an object and a section image of the object is produced on the basis of a received signal, the signal is processed to produce a two-dimensional elasticity image of an elasticity value representing elasticity, volume data is produced from a plurality of the two-dimensional elasticity images, elasticity value data of the volume data included in a desired elasticity value range is selected and rendered to produce a three-dimensional elasticity image of the elasticity value data in the elasticity value range, and the three-dimensional elasticity image and at least one of the two-dimensional elasticity image and the section image showing an area corresponding to the elasticity value range are displayed.

The ultrasonic diagnostic apparatus has the mode in which the operator sets the elasticity value range to be rendered (rendering range) and the image is displayed so as to allow the operator to easily recognize the area of the elasticity value range. The mode is realized by the image system control unit 44 controlling the respective components as shown in a flow of FIG. 5.

When the operator selects the mode on the operation panel 120, the image system control unit 44 reads and executes a program stored in a built-in memory to perform the control as described below.

First, at step 61, the monochrome section image 111 produced by the section image constituting unit 7 or the multi-frame constituting unit 46 is, combined with the two-dimensional elasticity image 112 produced by the two-dimensional elasticity image constituting unit 34 or the multiframe constituting unit 48 in the switching and adding unit 12 with the above expressions (7) to (12) to produce the combined image. The combined image is displayed on the left area on the screen 100 in the image display unit 13 as shown in FIG. 2(a). At the same time, the elasticity value range predefined as the initial value is set in the rendering range setting unit 51 to cause the volume rendering unit 42 to produce the three-dimensional elasticity image of the voxels within the elasticity value range of the initial value. This image is displayed on the right area on the screen 100. At this point, the elasticity value range of the predefined initial value is displayed in the area 107 showing the elasticity value range in the lower portion on the screen 100 as shown in FIG. 2(c). By way of example, FIG. 2(c) shows the case where the elasticity value α of the initial value is 72 and the "hard" button is selected as the initial value in the soft/hard selecting switch 122, and the three-dimensional elasticity image 103 of the hard organ within the elasticity value range from 1 to 72 is displayed.

Next, the image system control unit 44 proceeds to step 62 and displays the area of the organ associated with the set elasticity value range (initial value) on the combined image in the left area on the screen 100. Specifically, the mask is placed on the two-dimensional elasticity image 112 of the combined image and the combination ratio of the two-dimensional elasticity image 112 is set to be lower than the setting ratio in the expressions (10) to (12) to show in which area on the two-dimensional elasticity image the set elasticity value range from 1 to 72 is present. This processing will be specifically described in the following.

The rendering range setting unit 51 outputs the elasticity value range from 1 to α (initial value) to the two-dimensional elasticity image constituting unit 34 or the multiframe constituting unit 48 producing the displayed two-dimensional elasticity image. The two-dimensional elasticity image constituting unit 34 or the multiframe constituting unit 48 sets the elasticity value of the two-dimensional elasticity image at coordinates (x,y)(x=0 to X, y=0 to Y) to E(x,y) and then extracts the area outside the set elasticity value range (1 to a) with the expressions (13) and (14) to produce a mask (M1) 110 (see FIG. 6).

When $1 \leq E(x,y) \leq \alpha$, then $M1(x,y)=1$    expression (13)

When $\alpha < E(x,y)$, then $M1(x,y)=0$    expression (14)

In combining the monochrome section image 111 with the two-dimensional elasticity image 112, the switching and adding unit 12 adds them at the combination ratio of the masked area of the two-dimensional elasticity image 112 lower than the set ratio r based on the mask (M1) 110 to produce and display the masked combined image as shown in FIG. 6(b).

The output values D(R)(x,y), D(G)(x,y), and D(B)(x,y) of a pixel in the masked combined image are determined with the following expressions (15) to (20). It should be noted that the output values of red (R), green (G), and blue (B) of a pixel at coordinates (x,y) in the color two-dimensional elasticity image are set at E(R)(x,y), E(G)(x,y), and E(B)(x,y), and the output values of red (R), green (G), and blue (B) of a pixel at coordinates (x,y) after the monochrome section image is converted into the color section image are set at C(R)(x,y) C(G)(x,y), and C(B)(x,y), where r represents the combination ratio (0<r≤1) set by the operator, and w is a predefined weight (0≤w≤1).

When $M1(x,y)=1$, then $D(R)(x,y)=E(R)(x,y) \times r + C(R)(x,y)$   expression (15)

$D(G)(x,y)=E(G)(x,y) \times r + C(G)(x,y)$   expression (16)

$D(B)(x,y)=E(B)(x,y) \times r + C(B)(x,y)$   expression (17)

When $M1(x,y)=0$, then $D(R)(x,y)=E(R)(x,y) \times r \times w + C(R)(x,y)$   expression (18)

$D(G)(x,y)=E(G)(x,y) \times r \times w + C(G)(x,y)$   expression (19)

$D(B)(x,y)=E(B)(x,y) \times r \times w + C(B)(x,y)$   expression (20)

Thus, in the displayed combined image, as shown in FIG. 6(b), the color two-dimensional elasticity image 112 is displayed in a darker color in an area 108 over which the mask (M1) 110 is not placed. The two-dimensional elasticity image 112 is displayed in a lighter color and the monochrome section image 111 is displayed in a darker color in the area over which the mask (M1) 110 is placed outside the area 108. This allows the operator to intuitively and easily recognize that the area of the two-dimensional elasticity image 112 displayed in the darker color is the area corresponding to the three-dimensional elasticity image 103 in the right portion on the screen 100.

Next, the image system control unit 44 proceeds to step 63 and receives from the operator through the interface unit 43 the setting of the elasticity value range for which the operator wishes to display the three-dimensional elasticity image. Specifically, the operator rotates the toggle switch 121 shown in FIG. 3(a) to change the elasticity value α from the initial value α=72 to α=50 as shown in FIG. 3(b) and FIG. 3(c). The image system control unit 44 receives the elasticity value α=50 and receives the setting of the button selected in the soft/hard selecting switch 122. For example when the "hard" button is selected, the image system control unit 44 receives the setting of the elasticity value range from 1 to 50.

Figure 3:
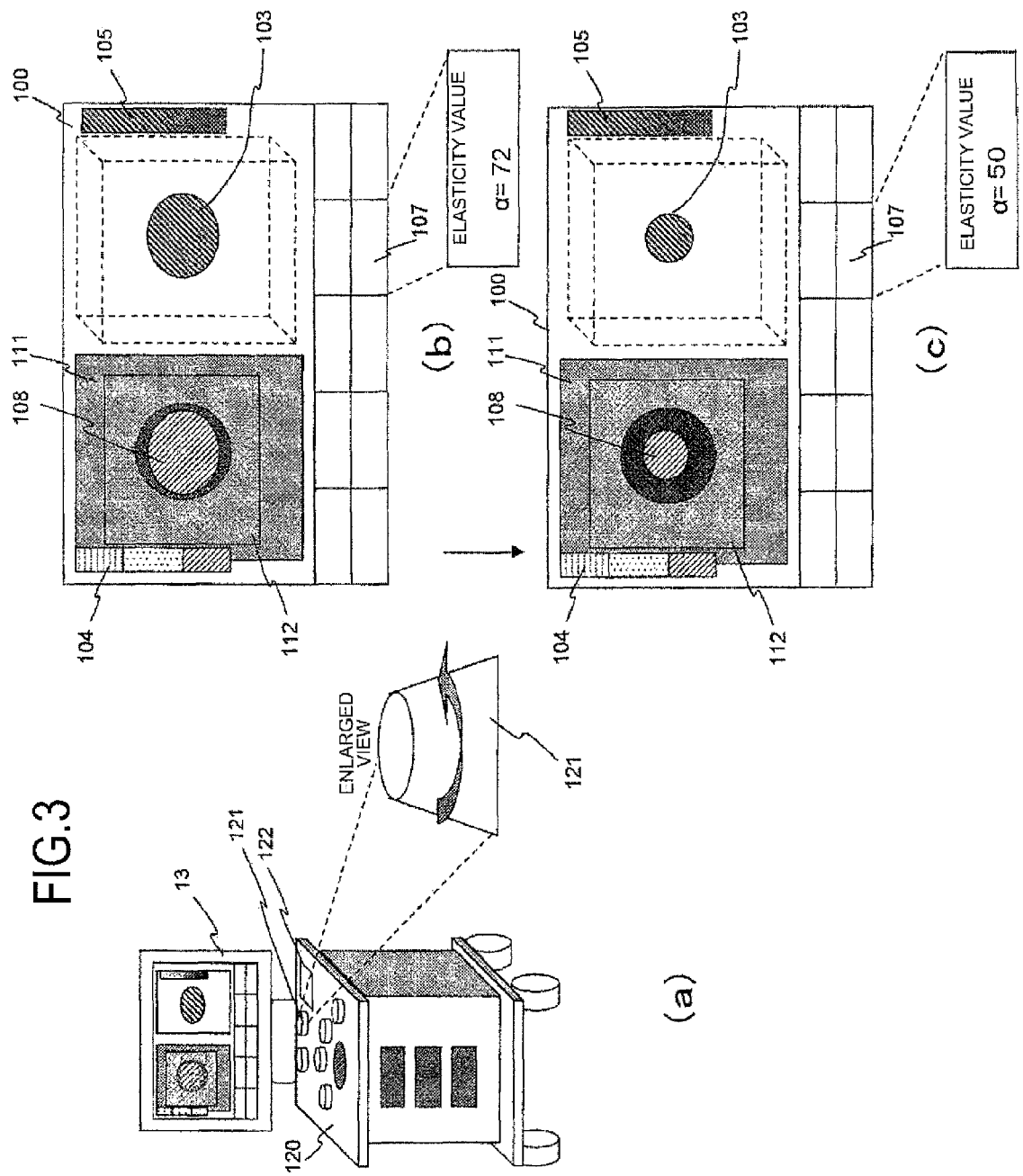
FIG. 3 (a) A perspective view showing the outer appearance of an image display unit 13 and an operation panel 120 in the ultrasonic diagnostic apparatus of FIG. 1 and an enlarged view of a toggle switch 121 on the operation panel 120, (b) an explanatory view showing an example of the screen when an elasticity value α is set at 72 with the toggle switch 121 in Embodiment 1, and (c) an explanatory view showing an example of the screen when the elasticity value α is set at 50 with the toggle switch 121 in Embodiment 1.
Figure 4:
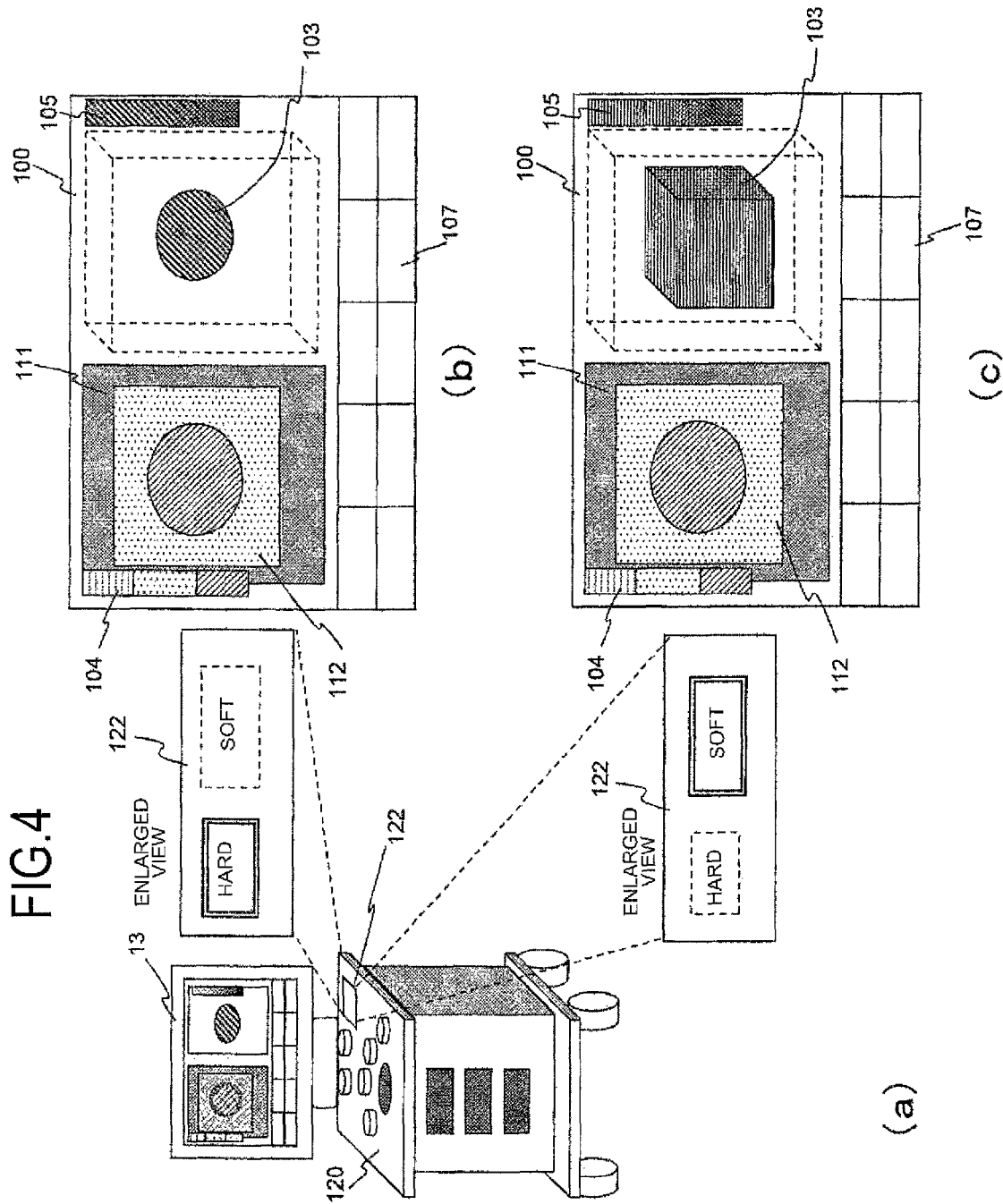
FIG. 4 (a) A perspective view showing the outer appearance of the image display unit 13 and the operation panel 120 in the ultrasonic diagnostic apparatus of FIG. 1 and an enlarged view of a soft/hard selecting switch 122 on the operation panel 120, (b) an explanatory view showing an example of the screen when a "hard" button is selected in the soft/hard selecting switch 122 in the embodiment, and (c) an explanatory view showing an example of the screen when a "soft" button is selected in the soft/hard selecting switch 122 in the embodiment.

The image system control unit 44 proceeds to step 64 and performs control such that the volume rendering unit 42 renders the voxels within the elasticity value range from 1 to α (that is, 1 to 50) set as the rendering range to produce and display the three-dimensional elasticity image in the right area on the screen 100 as shown in FIG. 3(*c*). In the display example of FIG. 3(*c*), the three-dimensional elasticity image including only the harder organ (within the range of the smaller elasticity values) than that in the display example of FIG. 3(*b*) is shown.

At step 65, the mask (M1) 110 is produced similarly to step 62 for the elasticity value range from 1 to α (that is, 1 to 50) received at step 63, the mask (M1) is placed on the two-dimensional elasticity image 112 of the combined image, the addition ratio of the two-dimensional elasticity image 112 in the area outside the elasticity value range set as the rendering range is reduced with the weight w to produce the combined image at the increased addition ratio of the monochrome section image, and the produced combined image is displayed in the left area on the screen 100.

As a result, in the displayed combined image shown in FIG. 3(*c*), the area 108 over which the mask (M1) 110 is not placed is smaller than that in FIG. 3(*b*). This allows the operator to intuitively and easily recognize that the organ corresponding to the three-dimensional elasticity image 103 in the right portion on the screen 100 is represented in the area 108 of the color two-dimensional elasticity image 112 displayed in a darker color. Thus, when the operator manipulates the toggle switch 121 to change the elasticity value range, the operator can recognize that the area 108 of the color two-dimensional elasticity image 112 displayed in the darker color is changed (that the inner area reduced in size is the harder area in the example of FIG. 3(*b*) and FIG. 3(*c*)).

The image system control unit 44 returns to step 63, and performs steps 64 to 65 when it receives a change in the elasticity value range from the next operator.

As described above, in Embodiment 1, the three-dimensional elasticity image provided by rendering only the voxels within the elasticity value range desired by the operator is displayed in parallel to the two-dimensional combined image, and the area associated with the elasticity value range of the three-dimensional elasticity image can be displayed with the mask placed on the two-dimensional combined image. This can provide the ultrasonic diagnostic apparatus capable of displaying the three-dimensional elasticity image including only the area within the desired elasticity value range and allowing the operator to easily recognize the position of that area.

While Embodiment 1 includes putting the weight with the value w to place the mask in the expressions (18) to (20), w may be a fixed value or the value of w may be received from the operator. While Embodiment 1 employs the range of 0≤w≤1 for w, the value of w higher than 1 may be used to display the two-dimensional elasticity image of the area outside the elasticity value range set as the rendering range in a darker color.

Alternatively, processing may be added to reduce the combination ratio of the area outside the elasticity value range set as the rendering range within the switching and adding unit 12 without creating the mask.

While Embodiment 1 includes displaying the combined image with the mask placed thereon while the initial value and the elasticity value range are set at steps 62 and 65, step 62 may not be performed, that is, the mask may not be placed on the combined image when the initial value of the elasticity value range is used, and only when the setting of the elasticity value range is received from the operator at step 63, the mask may be placed on the combined image at step 65.

Figure 2:
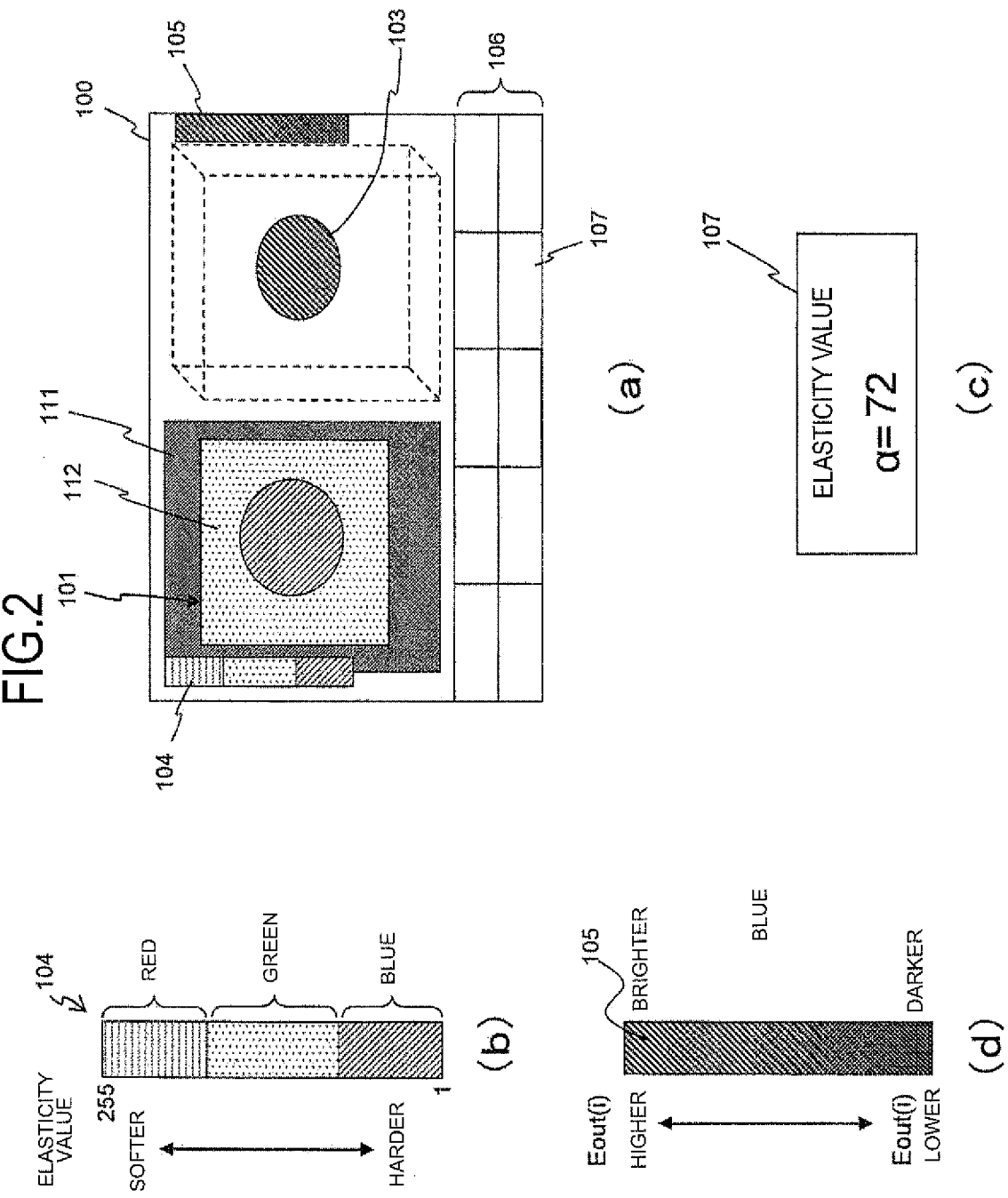
FIG. 2 (a) An explanatory view showing an example of a screen on which a combined image of a monochrome section image 111 and a color two-dimensional elasticity image 112 and a three-dimensional elasticity image are displayed in the ultrasonic diagnostic apparatus of FIG. 1, (b) an enlarged view of a color map 104 in the screen example of FIG. 2(a), (c) an enlarged view of a display area of an elasticity value range in FIG. 2(a), and (d) an enlarged view of a color map 105 in the screen example of FIG. 2(a).

In this case, the time period during which the combined image is displayed with the mask placed thereon at step 65 may be set only at the time period during which the toggle switch 121 is manipulated or only at a predetermined limited time period after the toggle switch 121 is manipulated. Specifically, the combined image with the mask placed thereon may be displayed in accordance with the value of the toggle switch 121 in the limited time period such as the time period during which the operator rotates the toggle switch 121, and the normal combined image produced with the expressions (10) to (12) as shown in FIG. 2(*a*) may be displayed without placing the mask in the time period during which the toggle switch 121 is not rotated (before and after the setting of the elasticity value range). With the display of the combined image with the mask placed thereon only in the time period during which the operator rotates the toggle switch 121, the operator can easily recognize in which area on the combined image the elasticity value range being set is present during the adjustment of the setting range of the elasticity value. In addition, after the completion of the manipulation of the toggle switch 121, the operator can advantageously recognize the section shape and the overall two-dimensional elasticity image in the normal combined image including the overall two-dimensional elasticity image.

While Embodiment 1 described above includes placing the mask on the two-dimensional elasticity image 112 of the combined image to display the elasticity value range set as the rendering range, the two-dimensional elasticity image may not be displayed, and the mask produced with the two-dimensional elasticity image may be placed on the monochrome section image to show the rendering range on the monochrome section image. Alternatively, the monochrome elasticity image may not be combined for display, and the masked two-dimensional elasticity image and the three-dimensional elasticity image may be displayed side by side.

Embodiment 2

In Embodiment 2, the area outside the elasticity value range set as the rendering range is transparently displayed in the two-dimensional elasticity image of the combined image displayed in the left area on the screen 100 as shown in FIG. 7.

Figure 5:
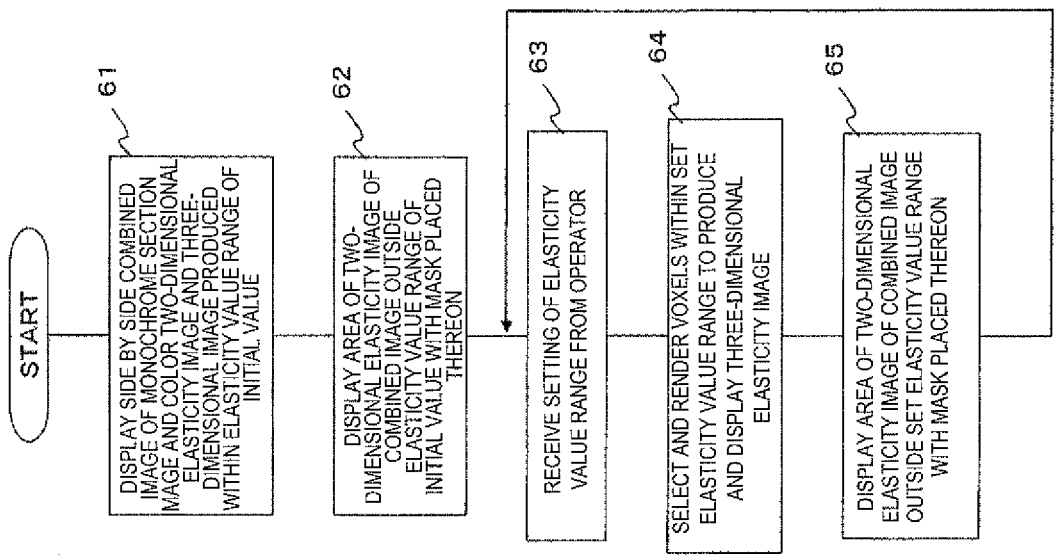
FIG. 5 A flow chart showing the operation in a mode in Embodiment 1.

Specifically, the following expressions (21) to (26) are used in putting the weight on the two-dimensional elasticity image with the mask M1($x,y$) at steps 62 and 64 of FIG. 5 in Embodiment 1.

When M1($x,y$)=1, then $$D(R)(x,y)=E(R)(x,y) \times r+C(R)(x,y) \quad \text{expression (21)}$$

$$D(G)(x,y)=E(G)(x,y) \times r+C(G)(x,y) \quad \text{expression (22)}$$

$$D(B)(x,y)=E(B)(x,y) \times r+C(B)(x,y) \quad \text{expression (23)}$$

when M1($x,y$)=0, then $$D(R)(x,y)=C(R)(x,y) \quad \text{expression (24)}$$

$$D(G)(x,y)=C(G)(x,y) \quad \text{expression (25)}$$

$$D(B)(x,y)=C(B)(x,y) \quad \text{expression (26)}$$

As apparent from the expressions (24) to (26), the two-dimensional elasticity image 112 is not combined in the area (the area of M1($x,y$)=0) outside the elasticity value range set as the rendering range, so that the two-dimensional elasticity image 112 is displayed only in the area corresponding to the elasticity value range set as the rendering range as shown in FIG. 7. In the area outside the elasticity value range set as the rendering range, the two-dimensional elasticity image is not displayed but the (transparent) combined image is obtained.

Since the other configurations are similar to those in Embodiment 1, the description thereof is omitted.

Embodiment 3

In Embodiment 3, at steps 62 and 65 of FIG. 5 in Embodiment 1, the combined image is produced by filling in the area of the elasticity value range set as the rendering range with a predetermined single color corresponding to the elasticity value of that area.

Specifically, the following expressions (27) to (32) are used in putting the weight on the two-dimensional elasticity image with the mask M1($x,y$) 110 as shown in FIG. 8(*a*) at steps 62 and 64 in Embodiment 1.

When M1($x,y$)=1, then $$D(R)(x,y)=K(R)(x,y) \qquad \text{expression (27)}$$

$$D(G)(x,y)=K(G)(x,y) \qquad \text{expression (28)}$$

$$D(B)(x,y)=K(B)(x,y) \qquad \text{expression (29)}$$

When M1($x,y$)=0, then $$D(R)(x,y)=E(R)(x,y) \times r \times w + C(R)(x,y) \qquad \text{expression (30)}$$

$$D(G)(x,y)=E(G)(x,y) \times r \times w + C(G)(x,y) \qquad \text{expression (31)}$$

$$D(B)(x,y)=E(B)(x,y) \times r \times w + C(B)(x,y) \qquad \text{expression (32)}$$

K(R), K(G), and K(B) represent hues predefined in accordance with the elasticity values of the elasticity value range (M1($x,y$)=1) set as the rendering range. For example, when the elasticity value range set as the rendering range is a predetermined hard elasticity value range, the area is filled in with a blue tone color not present in the elasticity image color map 105, and when the range is a soft area, the area is filled in with a red tone color not present in the elasticity image color map 105. Any color other than red and blue may be used.

The hardness (elasticity value) of the elasticity value range set as the rendering range is calculated from the elasticity value E(i) of the voxel included in the elasticity value range set as the rendering range out of the elasticity volume data. For example, the average value, the maximum value, or the minimum value is calculated and used.

This provides the advantage that the area 108 of the elasticity value range set as the rendering range is filled in with the single color not present in the color map 105 in the combined image displayed in the left area on the screen 100 as shown in FIG. 8(*a*), so that the shape and the size of the area 108 are easily recognized.

Since the other configurations are similar to those in Embodiment 1, the description thereof is omitted. It should be noted that the time to fill in the area 108 with the predetermined single color may also be limited to the time period such as the time period during which the operator manipulates the toggle switch 121 in the present embodiment. This is particularly effective since the two-dimensional elasticity image can be seen in the normal display in the time period during which the toggle switch 121 is not manipulated.

The area outside the elasticity value range set as the rendering range may not be displayed with the weight from the expressions (30) to (32), and instead the two-dimensional elasticity image may be transparent with the expressions (24) to (26) in Embodiment 2.

While Embodiment 3 includes filling in the area 108 of the elasticity value range set as the rendering range with the single color, the area outside the elasticity value range set as the rendering range may be fill in with a single color with the following expressions (33) to (38). The area 108 of the elasticity value range set as the rendering range is displayed with a weight value w.

When M1($x,y$)=1, then $$D(R)(x,y)=E(R)(x,y) \times r \times w + C(R)(x,y) \qquad \text{expression (33)}$$

$$D(G)(x,y)=E(G)(x,y) \times r \times w + C(G)(x,y) \qquad \text{expression (34)}$$

$$D(B)(x,y)=E(B)(x,y) \times r \times w + C(B)(x,y) \qquad \text{expression (35)}$$

When M1($x,y$)=0, then $$D(R)(x,y)=K(R)(x,y) \qquad \text{expression (36)}$$

$$D(G)(x,y)=K(G)(x,y) \qquad \text{expression (37)}$$

$$D(B)(x,y)=K(B)(x,y) \qquad \text{expression (38)}$$

Embodiment 4

Next, Embodiment 4 is described with reference to FIG. 9(*a*) and FIG. 9(*b*). In Embodiment 4, a line 116 representing the outline of the rendering range (elasticity value range) is displayed on the two-dimensional elasticity image 112 of the combined image.

Specifically, at steps 62 and 65 of FIG. 5 in Embodiment 1, the combined image is produced by combining the line 116 representing the outer periphery of the area of the elasticity value range set as the rendering range and is displayed as shown in FIG. 9(*b*). At steps 62 and 65, the rendering range setting unit 51 outputs the initial value or the elasticity value α set by the operator with the toggle switch 121 to the two-dimensional elasticity image constituting unit 34 or the multiframe constituting unit 48. The two-dimensional elasticity image constituting unit 34 or the multiframe constituting unit 48 produces a mask (M2) 115 shown in FIG. 9(*a*) with the expressions (39) and (40).

$$\text{When } \alpha-T \leq E(x,y) \leq \alpha+T, \text{ then } M2(x,y)=1 \qquad \text{expression (39)}$$

$$\text{When } E(x,y) < \alpha-T, \alpha+T < E(x,y), \text{ then } M2(x,y)=0 \qquad \text{expression (40)}$$

T represents a predefined value, and 2T corresponds to the line width of the line 116 representing the outline of the rendering range. For example, when T is set at two, the line width of the line 116 is four as the elasticity value.

The value of T may be previously defined, or the value received from the operator through the interface unit 43 may be used.

When the switching and adding unit 12 combines the monochrome section image 111 with the two-dimensional elasticity image 112 at steps 62 and 65, the switching and adding unit 12 allocates a predetermined hue, for example black color, as the output value of the pixel in the area of M2($x,y$)=1 based on the mask M2($x,y$) 115. For the pixel value in the area of M2($x,y$)=0, the normal combined image is used with the above expressions (10) to (12).

Since this can draw the outline of the area 108 of the rendering range in the black color with the line 116 as shown in FIG. 9(*b*) in the two-dimensional elasticity image of the combined image, the operator can easily recognize in which area the rendering range (elasticity value range) of the three-dimensional elasticity image is present on the combined image.

The hue of the line 116 may be previously defined or may be received from the operator through the interface unit 43.

Since the other configurations are similar to those in Embodiment 1, the description thereof is omitted. It should be noted that the time to draw the line 116 representing the outline may also be limited to the time period such as the time period during which the operator manipulates the toggle switch 121 in the present embodiment. This is particularly effective since the two-dimensional elasticity image can be seen in the normal display in the time period during which the toggle switch 121 is not manipulated.

Embodiment 5

Figure 10:
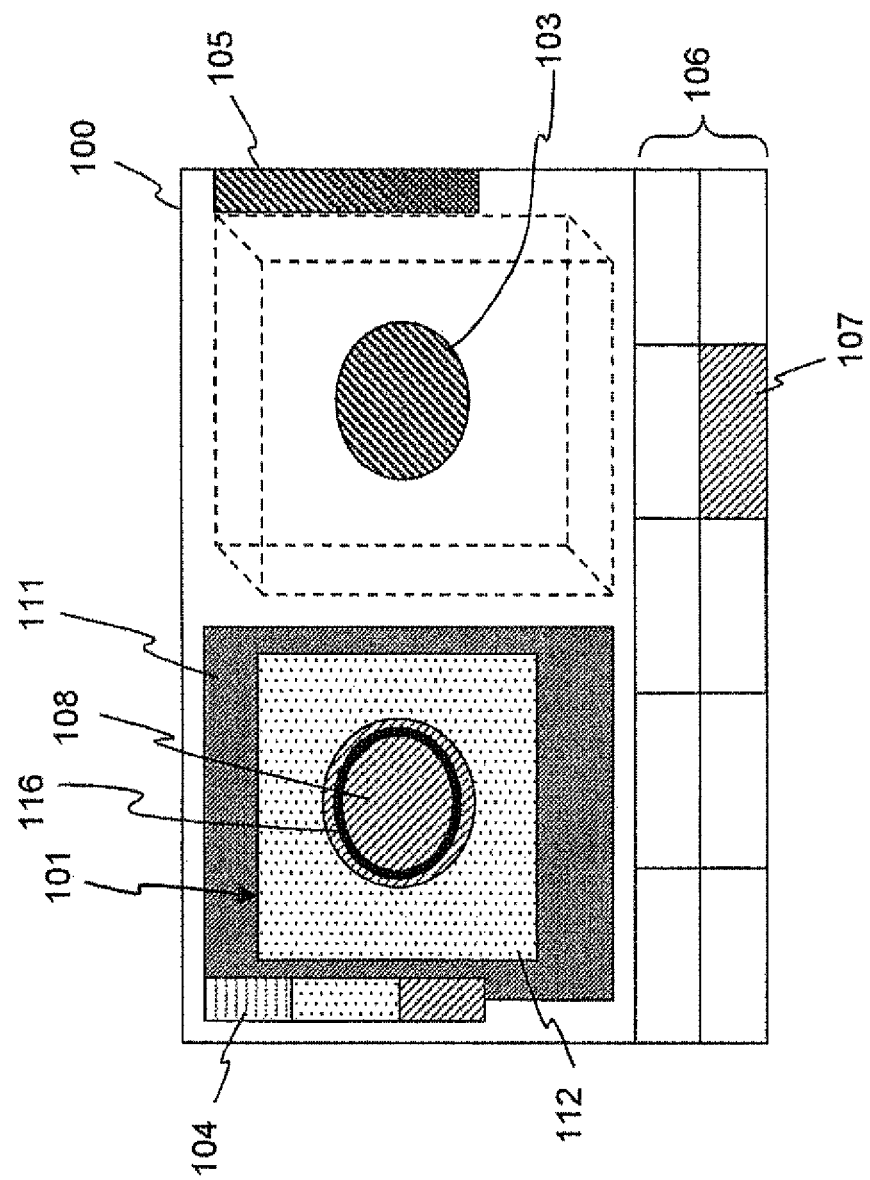
FIG. 10 An explanatory view showing an example of the screen produced in Embodiment 5.

Next, Embodiment 5 is described with reference to FIG. 10.

In Embodiment 5, the background color of the area 107 of the elasticity value α on the screen 100 set by the operator as the rendering range is displayed with a hue corresponding to the elasticity value α on the color map 104. The control of the display is performed by the rendering range setting unit 51.

The operator can see not only the numeric value displayed in the area 107 but also the background color of the area 107 while rotating the toggle switch 121 to easily recognize which area on the two-dimensional elasticity image 112 the elasticity value α set as the upper limit or the lower limit of the rendering range corresponds to.

Embodiment 5 may be implemented together with the display of the combined image in any of Embodiments 1 to 4. In this case, the operator can recognize the range of the elasticity values set as the rendering range with both the combined image and the background color of the area 107. In the example of FIG. 10, the background color of the area 107 is displayed with the hue corresponding to the elasticity value α in addition to the display of the outline 116 in Embodiment 4.

Instead of the background color of the area 107, the character "elasticity value α=00" displayed in the area 107 may be shown with the hue corresponding to the elasticity value α.

It should be noted that the time to display the background color or the character color in the area 107 with the hue corresponding to the elasticity value α may also be limited to the time period such as the time period during which the operator manipulates the toggle switch 121 in the present embodiment. This is particularly effective since the operator can concentrate on the display other than the area 107 while the toggle switch 121 is not manipulated.

Embodiment 6

Next, Embodiment 6 is described with reference to FIG. 11.

In Embodiment 6, a mask 117 is placed on the area outside the elasticity value range set as the rendering range on the color map 104 to be opaque or to reduce the intensity, or the area of the mask 117 on the color map 104 is shown transparently and is not displayed. The control of the display is performed by the rendering range setting unit 51.

Embodiment 6 is implemented together with the display of the combined image in any of Embodiments 1 to 4. This allows the operator to recognize the range of the elasticity values set as the rendering range with both the combined image and the display of the color map 104. Embodiment 6 may be performed together with the display of the background color or the character color of the area 107 in Embodiment 5.

Figure 11:
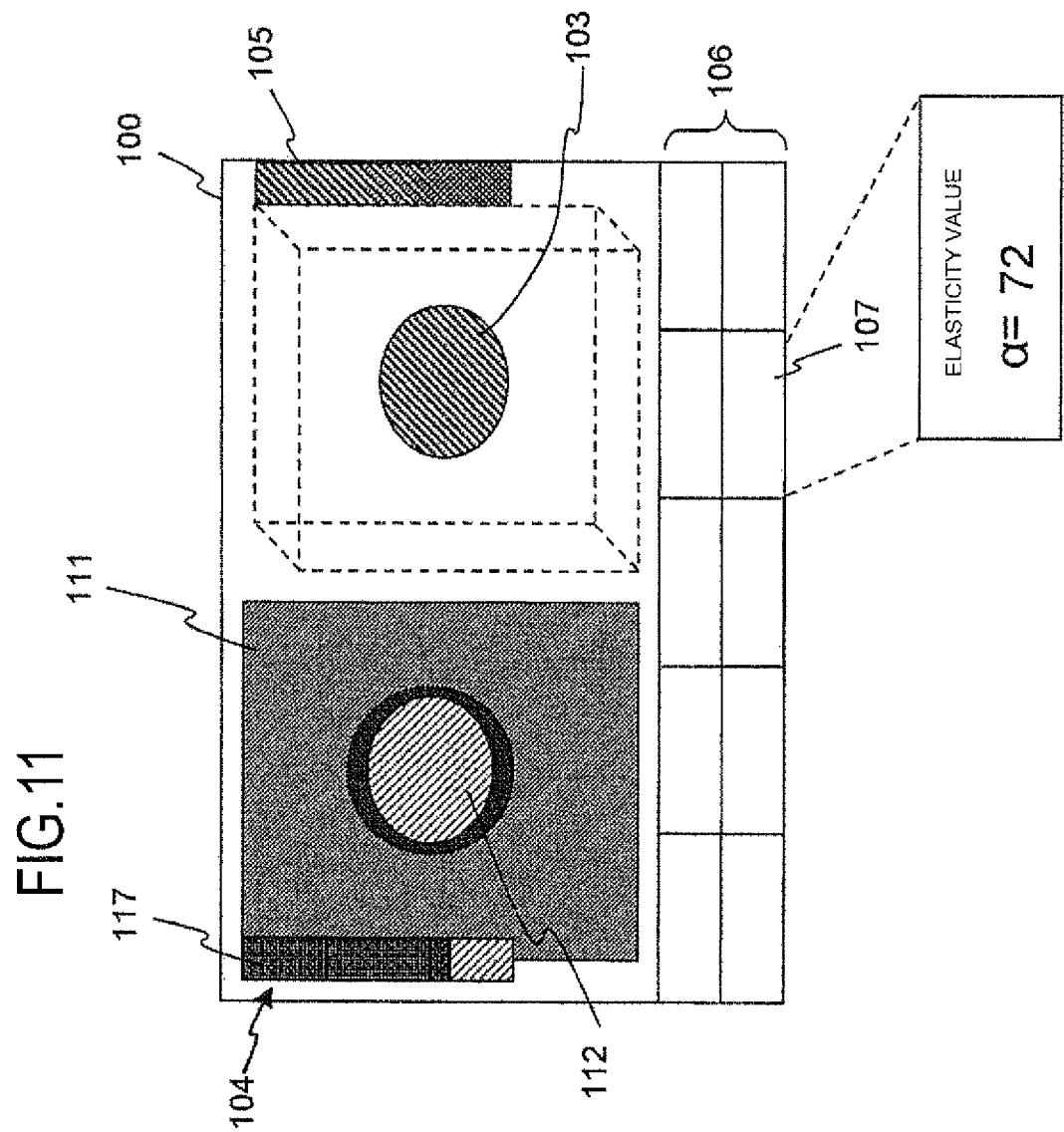
FIG. 11 An explanatory view showing an example of the screen produced in Embodiment 6.

The example of FIG. 11 shows the screen 100 on which the combined image in Embodiment 2 is displayed and the mask 117 is placed on the color map 104.

The operator can see not only the elasticity value displayed in the area 107 but also the color map 104 while rotating the toggle switch 121 to easily recognize the elasticity value range set as the rendering range.

The processing of placing the mask 117 may be performed not only on the color map 104 for the two-dimensional elasticity image but also on the color map 105 for the three-dimensional elasticity image.

In addition, the operator can set a plurality of elasticity value ranges such that the plurality of elasticity value ranges are displayed simultaneously by placing the mask 117 on the color map 104 or the like.

It should be noted that the time to place the mask on the color map 104 or the like may also be limited to the time period during which the operator manipulates the toggle switch 121 in the present embodiment. Since this prevents the placement of the mask while the switch is not manipulated, the operator can visually recognize the overall color map 104.

Embodiment 7

Next, Embodiment 7 is described with reference to FIG. 12(*a*) and FIG. 12(*b*).

Figure 12:
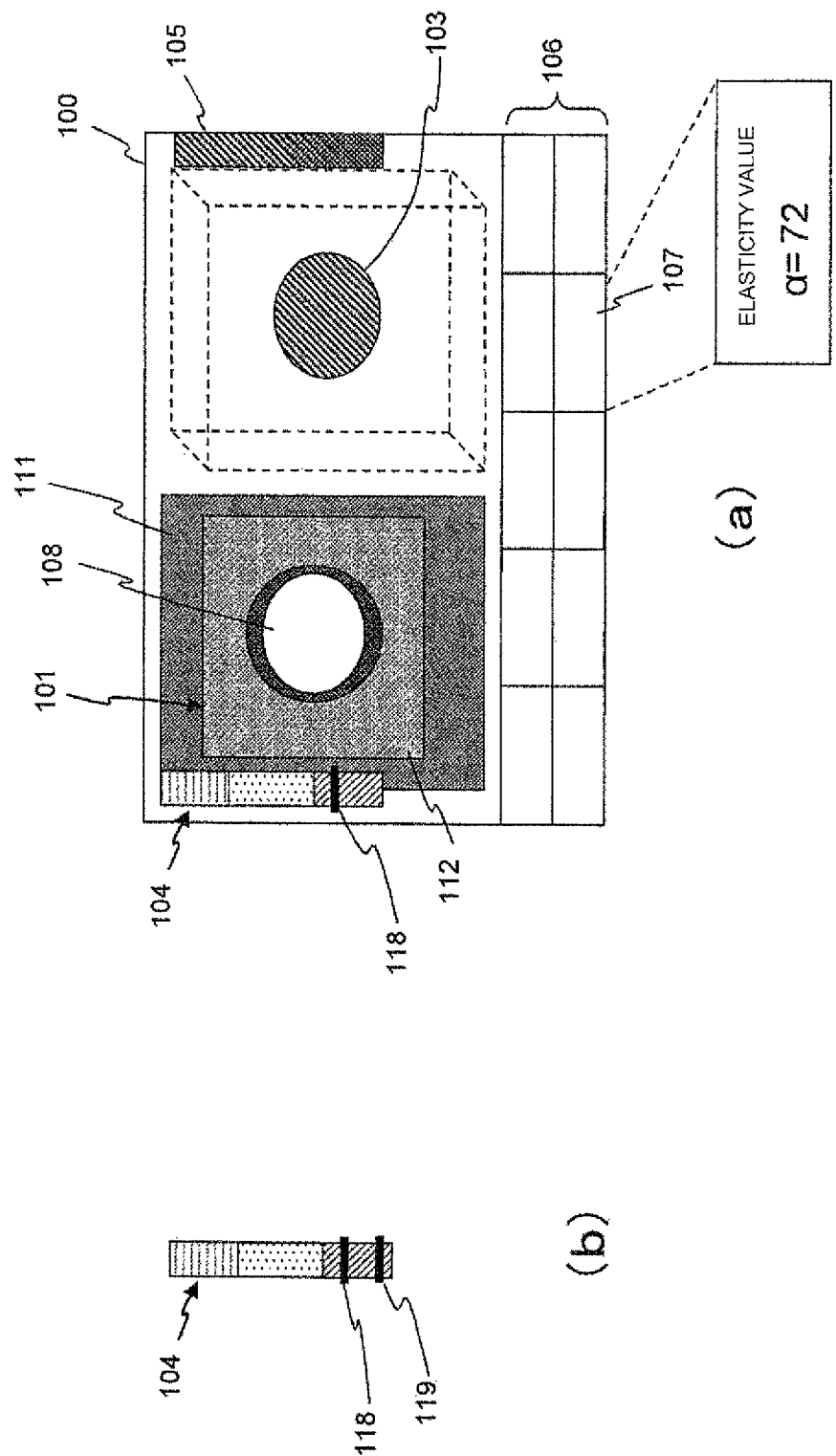
FIG. 12 (a) An explanatory view showing an example of the screen produced in Embodiment 7, and (b) an enlarged view of the color map in FIG. 12(a).

In Embodiment 7, a bar 118 is displayed at the position of the elasticity value α set as the upper limit or the lower limit of the rendering range on the color map 104 to indicate the elasticity value α to the operator as shown in FIG. 12(*a*). The control of the display is performed by the rendering range setting unit 51.

Embodiment 7 is implemented together with the display of the combined image in any of Embodiments 1 to 4. This allows the operator to recognize the range of the elasticity values set as the rendering range with both the combined image and the display of the bar 118 on the color map 114. In addition, Embodiment 7 may be performed together with the display of the background color or the character color of the area 107 in Embodiment 5.

The example of FIG. 12(*a*) shows the screen 100 on which the combined image in Embodiment 3 is displayed and the bar 118 is displayed on the color map 104.

The numeric value of the elasticity value α shown by the bar 118 may be displayed near the bar 118.

The color map on which the bar is displayed is not limited to the color map 104 for the two-dimensional elasticity image. The bar 118 may be displayed on the color map 105 for the three-dimensional elasticity image.

The operator may set both the upper limit and the lower limit of the elasticity value range without using the soft/hard selecting switch 122, and the upper limit and the lower limit of the elasticity value range may be displayed by two bars 118 and 119 as shown in FIG. 12(*b*). In this case, the operator may set a plurality of elasticity value ranges such that the upper limits and the lower limits of the plurality of elasticity value ranges are displayed simultaneously by a plurality of sets of bars 118 and 119. In this case, the set of the bars 118 and 119 for each of the elasticity value ranges may have a different color.

It should be noted that the time to display the bar 118 or the like on the color map 104 or the like may also be limited to the time period during which the operator manipulates the toggle switch 121 in the present embodiment. Since the bar 118 or the like is not displayed while the switch is not manipulated, the operator can concentrate on the display of the image.

DESCRIPTION OF REFERENCE NUMERALS AND SIGNS

1 OBJECT, 2 PROBE, 3 TRANSMITTING UNIT, 4 RECEIVING UNIT, 5 ULTRASONIC TRANSMISSION/RECEPTION CONTROL UNIT, 6 PHASING AND ADDING UNIT, 7 SECTION IMAGE CONSTITUTING UNIT, 12 SWITCHING AND ADDING UNIT, 13 IMAGE DISPLAY UNIT, 27 RF SIGNAL FRAME DATA STORAGE UNIT, 28 RF SIGNAL FRAME DATA SELECTING UNIT, 30 DISPLACEMENT MEASURING UNIT, 32 ELASTICITY INFORMATION CALCULATING UNIT, 34 TWO-DIMENSIONAL ELASTICITY IMAGE CONSTITUTING UNIT, 36 SECTION IMAGE VOLUME DATA CREATING UNIT, 38 VOLUME RENDERING UNIT, 39 TWO-DIMENSIONAL ELASTICITY IMAGE STORAGE UNIT, 40 ELASTICITY IMAGE VOLUME DATA CREATING UNIT, 42 VOLUME RENDERING UNIT, 43 INTERFACE UNIT, 44 IMAGE SYSTEM CONTROL UNIT, 45 SHORT AXIS SCAN POSITION CONTROL UNIT, 46 MULTIFRAME CONSTITUTING UNIT (SECTION IMAGE), 48 MULTIFRAME CONSTITUTING UNIT (ELASTICITY IMAGE), 51 RENDERING RANGE SETTING UNIT, 100 SCREEN, 101 ROI, 103 THREE-DIMENSIONAL ELASTICITY IMAGE, 104 COLOR MAP (TWO-DIMENSIONAL ELASTICITY IMAGE), 105 COLOR MAP (THREE-DIMENSIONAL ELASTICITY IMAGE), 106 PARAMETER DISPLAY AREA, 107 AREA SHOWING ELASTICITY VALUE a IN RENDERING RANGE, 111 MONOCHROME SECTION IMAGE, 112 COLOR TWO-DIMENSIONAL ELASTICITY IMAGE, 120 OPERATION PANEL, 121 TOGGLE SWITCH, 122 SOFT/HARD SELECTING SWITCH

The invention claimed is:

1. An ultrasonic diagnostic apparatus comprising:
   an ultrasonic probe which transmits an ultrasonic wave to an object to be examined and receives a reflected echo signal from the object; and
   an ultrasonic diagnostic system comprising circuitry, memory, a display and an input device to perform operations to:
   transmit ultrasonic waves into the object via the ultrasonic probe;
   produce a section image of the object based on the reflected echo signal via the ultrasonic probe;
   process the reflected echo signal to produce a two-dimensional elasticity image of an elasticity value representing elasticity;
   produce volume data formed of a plurality of the two-dimensional elasticity images;
   select and render elasticity value data of the volume data included in a desired elasticity value range to produce a three-dimensional elasticity image of the elasticity value data in the elasticity value range;
   display the three-dimensional elasticity image and at least one of the two-dimensional elasticity image and the section image showing an area corresponding to the elasticity value range;
   set the elasticity value range by the input device; and
   display the area corresponding to the elasticity value range on at least one of the two-dimensional elasticity image and the section image only for a predetermined time period based on the set the elasticity value range by the input device.

2. The ultrasonic diagnostic apparatus according to claim 1, wherein ultrasonic diagnostic system performs operations to display an area of the two-dimensional elasticity image outside the elasticity value range with a mask placed thereon.

3. The ultrasonic diagnostic apparatus according to claim 2, wherein the ultrasonic diagnostic system performs operations to display a combined image provided by adding the two-dimensional elasticity image and the section image at a ratio, the ratio in an area within the elasticity value range being different from the ratio in the area with the mask placed thereon.

4. The ultrasonic diagnostic apparatus according to claim 3, wherein the ultrasonic diagnostic system performs operations to display the combined image provided by adding the two-dimensional elasticity image at the ratio set at zero in the area with the mask placed thereon.

5. The ultrasonic diagnostic apparatus according to claim 2, wherein the ultrasonic diagnostic system performs operations to display an area of the two-dimensional elasticity image within the elasticity value range or the area with the mask placed thereon filled in with a single hue.

6. The ultrasonic diagnostic apparatus according to claim 5, wherein the single hue is set in accordance with an elasticity value in the area of the two-dimensional elasticity image to be filled in with the hue.

7. The ultrasonic diagnostic apparatus according to claim 1, wherein the ultrasonic diagnostic system performs operations to display a line representing an outline of the elasticity value range in the two-dimensional elasticity image.

8. The ultrasonic diagnostic apparatus according to claim 1, wherein the two-dimensional elasticity image is a color image having a different hue provided in accordance with an elasticity value, and the ultrasonic diagnostic system performs operations to display a color map representing the relationship between the elasticity value and the hue by adding a display showing the elasticity value range thereto.

9. The ultrasonic diagnostic apparatus according to claim 1, wherein the two-dimensional elasticity image is a color image having a different hue provided in accordance with an elasticity value, and the ultrasonic diagnostic system performs operations to display the elasticity value range with a numeric value by adding a hue corresponding to the elasticity value range thereto.

10. A method of displaying an ultrasonic image using an ultrasonic probe which transmits an ultrasonic wave to an object to be examined and receives a reflected echo signal from the object and an ultrasonic diagnostic system comprising circuitry, memory, a display and an input device, the method comprising:
    transmitting ultrasonic waves into the object via the ultrasonic probe;
    producing a section image of the object based on the reflected echo signal via the ultrasonic probe;
    processing the reflected echo signal to produce a two-dimensional elasticity image of an elasticity value representing elasticity;
    producing volume data from a plurality of the two-dimensional elasticity images;
    selecting and rendering elasticity value data of the volume data included in a desired elasticity value range to produce a three-dimensional elasticity image of the elasticity value data in the elasticity value range;
    displaying the three-dimensional elasticity image and at least one of the two-dimensional elasticity image and the section image showing an area corresponding to the elasticity value range;
    setting the elasticity value range by the input device; and
    displaying the area corresponding to the elasticity value range on at least one of the two-dimensional elasticity image and the section image only for a predetermined time period based on the set the elasticity value range by the input device.

11. The method of displaying an ultrasonic image according to claim 10, wherein the display step displays an area of the two-dimensional elasticity image outside the elasticity value range with a mask placed thereon.

12. The method of displaying an ultrasonic image according to claim 11, wherein the display step displays a combined image provided by adding the two-dimensional elasticity image and the section image at a ratio, the ratio in an area within the elasticity value range being different from the ratio in the area with the mask placed thereon.

13. The method of displaying an ultrasonic image according to claim 11, wherein the display step displays an area of the two-dimensional elasticity image within the elasticity value range or the area with the mask placed thereon filled in with a single hue.

14. The method of displaying an ultrasonic image according to claim 10, wherein the display step displays a line representing an outline of the elasticity value range in the two-dimensional elasticity image.

\* \* \* \* \*